(12) United States Patent
Champagne et al.

(10) Patent No.: US 8,529,611 B2
(45) Date of Patent: Sep. 10, 2013

(54) DISTAL INTERPHALANGEAL FUSION METHOD AND DEVICE

(75) Inventors: Lloyd Champagne, Paradise Valley, AZ (US); Bruce King, Tucson, AZ (US); Omar Contento, Hillsboro, OR (US); Mike Lanham, Tucson, AZ (US); Donald J. Martin, Tucson, AZ (US)

(73) Assignee: Competitive Global Medical, LLC, Tucson, AZ (US)

( * ) Notice: Subject to any disclaimer, the term of this patent is extended or adjusted under 35 U.S.C. 154(b) by 118 days.

(21) Appl. No.: 13/049,363

(22) Filed: Mar. 16, 2011

(65) Prior Publication Data
US 2011/0276099 A1 Nov. 10, 2011

Related U.S. Application Data

(60) Provisional application No. 61/314,317, filed on Mar. 16, 2010.

(51) Int. Cl.
*A61B 17/84* (2006.01)
*A61B 17/86* (2006.01)

(52) U.S. Cl.
USPC ........... 606/328; 606/301; 606/304; 606/306; 606/325

(58) Field of Classification Search
USPC ......... 606/300–321, 325, 328; 411/383–385, 411/388–389, 392, 396–397, 412; 403/339–340, 381
See application file for complete search history.

(56) References Cited

U.S. PATENT DOCUMENTS

| 2,390,461 | A | 12/1945 | Racz ............................... 138/89 |
| 4,119,092 | A | 10/1978 | Gil ............................. 128/92 D |
| 4,304,011 | A | 12/1981 | Whelan, III ..................... 3/1.91 |
| 4,352,212 | A | 10/1982 | Greene et al. .................... 3/1.91 |
| 4,759,768 | A | 7/1988 | Hermann et al. ................ 623/21 |
| 4,946,455 | A | 8/1990 | Rosen ........................... 604/403 |
| 5,011,497 | A | 4/1991 | Persson et al. .................. 623/21 |

(Continued)

FOREIGN PATENT DOCUMENTS

| EP | 1 632 200 | 3/2006 |
| FR | 2 651 119 | 8/1989 |

(Continued)

OTHER PUBLICATIONS

International Search Report and Written Opinion issued in PCT Application Serial No. PCT/US10/46870 on Oct. 20, 2010, 12 pgs.

(Continued)

*Primary Examiner* — Kevin T Truong
*Assistant Examiner* — Tracy Kamikawa
(74) *Attorney, Agent, or Firm* — Hayes Soloway P.C.

(57) ABSTRACT

A system, including methods, apparatus and kits for connecting bones and/or bone portions using a multi-part bone connector with one or more rotating joints is disclosed. A flexible bone fusion apparatus is provided having an anchor and a compressor, each of which engages with a coupler to provide axial and/or linear rotation of the apparatus. Alternatively, a compressor and an anchor may directly join with each other at a shared interface. Tools for installing and compressing the apparatus are provided. Also provided is a method for fusing two bones or bone portions to create a non-linear post-fusion orientation. A further aspect of the disclosure is a method for maintaining thread synchronization of a bone fusion apparatus having a discontinuous thread.

18 Claims, 17 Drawing Sheets

(56) References Cited

U.S. PATENT DOCUMENTS

| | | | |
|---|---|---|---|
| 5,074,882 A | 12/1991 | Grammont et al. | 623/23 |
| 5,129,903 A | 7/1992 | Luhr et al. | 606/71 |
| 5,147,386 A | 9/1992 | Carignan et al. | 623/21 |
| 5,251,520 A | 10/1993 | Lanham | 81/436 |
| 5,334,184 A | 8/1994 | Bimman | 606/63 |
| 5,417,692 A | 5/1995 | Goble et al. | 606/73 |
| 5,522,903 A | 6/1996 | Sokolow et al. | 623/21 |
| 5,569,247 A | 10/1996 | Morrison | 606/61 |
| 5,591,166 A | 1/1997 | Bernhardt et al. | 606/61 |
| 5,628,740 A | 5/1997 | Mullane | 606/61 |
| 5,667,510 A | 9/1997 | Combs | 606/86 |
| 5,683,466 A | 11/1997 | Vitale | 623/18 |
| 5,827,285 A | 10/1998 | Bramlet | 606/60 |
| 5,984,970 A | 11/1999 | Bramlet | 623/21 |
| 6,284,001 B1 | 9/2001 | Knapp | 623/21.14 |
| 6,689,169 B2 | 2/2004 | Harris | 623/21.16 |
| 6,733,502 B2 | 5/2004 | Altarac et al. | 606/61 |
| 6,767,351 B2 | 7/2004 | Orbay et al. | 606/69 |
| 6,780,186 B2 | 8/2004 | Errico et al. | 606/71 |
| 7,041,106 B1 | 5/2006 | Carver et al. | 606/72 |
| 7,608,096 B2 | 10/2009 | Foley et al. | 606/280 |
| 7,717,958 B2 | 5/2010 | Cragg et al. | 623/17.12 |
| 7,740,648 B2 | 6/2010 | Young et al. | 606/286 |
| 2002/0198527 A1 | 12/2002 | Muckter | 606/73 |
| 2004/0172031 A1 | 9/2004 | Rubecamp et al. | 606/73 |
| 2005/0055023 A1 | 3/2005 | Sohngen et al. | 606/62 |
| 2006/0235414 A1 | 10/2006 | Lim et al. | 606/73 |
| 2006/0271054 A1 | 11/2006 | Sucec et al. | 606/73 |
| 2007/0055236 A1 | 3/2007 | Hudgins et al. | 606/61 |
| 2007/0185584 A1 | 8/2007 | Kaufmann et al. | 623/21.15 |
| 2007/0270855 A1* | 11/2007 | Partin | 606/72 |
| 2007/0282342 A1 | 12/2007 | Niederberger et al. | 606/73 |
| 2008/0065224 A1 | 3/2008 | Reigstad et al. | 623/18.11 |
| 2008/0195156 A1 | 8/2008 | Ainsworth et al. | 606/279 |
| 2009/0062868 A1 | 3/2009 | Casutt | 606/316 |
| 2009/0112269 A1 | 4/2009 | Lieberman et al. | 606/301 |
| 2009/0210016 A1 | 8/2009 | Champagne | 606/309 |
| 2009/0234359 A1 | 9/2009 | Onoue et al. | 606/71 |
| 2009/0264934 A1 | 10/2009 | Youssef et al. | 606/280 |
| 2010/0036439 A1 | 2/2010 | Lavi | 606/308 |
| 2011/0004255 A1* | 1/2011 | Weiner et al. | 606/301 |

FOREIGN PATENT DOCUMENTS

| | | |
|---|---|---|
| FR | 2 692 776 | 6/1995 |
| WO | WO 95/33425 | 12/1995 |
| WO | WO 97/22301 | 6/1997 |
| WO | WO 02/30262 | 4/2002 |
| WO | WO 2005/041793 | 5/2005 |
| WO | WO 2010/026371 | 3/2010 |
| WO | WO 2010/047688 | 4/2010 |

OTHER PUBLICATIONS

International Search Report and Written Opinion issued in PCT Application Serial No. PCT/US11/028646 on May 3, 2011, 13 pgs.
International Search Report and the Written Opinion, dated Dec. 30, 2011 (10 pgs).

* cited by examiner

DISTAL INTERPHALANGEAL FUSION METHOD AND DEVICE

CROSS REFERENCE TO RELATED APPLICATIONS

This application claims priority to U.S. Provisional Application No. 61/314,317, filed Mar. 16, 2010, the contents of which are incorporated by reference herein in their entirety.

BACKGROUND

The embodiments of the invention disclosed herein generally relate to a medical device and medical procedure using that device, and more particularly, to a joint fusion assembly for arthroplastic convergence of opposing ends of bones.

Joint disorders, such as arthritis in the joints of digits, can be extremely painful. A common procedure to alleviate pain in such patients is to fixate the joint for fusion by arthrodesis. There are a number of arthrodesis techniques that promote fusion of adjacent bones of a digit (e.g., finger or toe). Historically, these techniques utilize a bone screw that draws the adjacent bones together at a 180 degree, or straight, angle. The digit then fuses at the joint in a fully-extended orientation. This fully-extended orientation of the digit in conventional arthrodesis techniques weakens grip strength and is often not esthetically pleasing to the patient. For example, the grip strength of the hand increases when the fingers can oppose each other as the hand grasps an object. If a finger is extended, it cannot properly oppose the other fingers to grasp the object, stabilize the object in the hand, or exert force on the object. Moreover, the digits of a human hand rest in a flexed position; therefore, a digit that is fused in an extended position looks abnormal and is not esthetically pleasing. Similarly, straight toe joints are unnatural and do not grip or fit properly within normal shoes.

One complication arising from the arthrodesis surgery is misalignment, or crooked, fusion at the joint. This can arise from imperfect alignment of the bone ends during surgery, subsequent misalignments caused by lateral impact during the healing process, or in the case of arthrodesis utilizing an implanted bone screw having a flexible joint, lateral rotation about the joint during healing. All three situations result in a digit that may heal in a different than desired orientation.

Accordingly, it would be an advantage to provide a joint assembly that overcomes the disadvantages of previous technology.

SUMMARY OF THE INVENTION

Embodiments of the invention are directed to an improved implantable bone fusion apparatus. Embodiments of the invention presented herein may be used in linear bone fusion repairs or in flexed or jointed applications. In a flexible bone fusion application, an embodiment of the invention is directed to a bone fusion apparatus comprising an anchor portion having an elongated body with screws threads on at least a portion of its exterior, the anchor having a leading tip and an end; a compressor portion having an elongated body with screw threads of the same pitch and diameter on at least a portion of its exterior; and a coupler having a first end adapted to rotatably engage the anchor in a first plane, the coupler also having a second end adapted to rotatably engage the compressor through axial rotation.

In a linear bone fusion application an embodiment of the invention is directed to a bone fusion apparatus comprising (a) an anchor portion comprising an elongated body with screw threads on at least a portion of its exterior, the anchor having a leading tip and a trailing end adapted for an axial rotation interface, the anchor trailing end also having a keyed driving pattern; (b) a compressor portion comprising an elongated body with screw threads of the same pitch and diameter on at least a portion of its exterior, the compressor having a trailing end and a leading end adapted for an axial rotation interface, the compressor leading end also having a keyed driving pattern different from the anchor trailing end keyed driving pattern; and (c) an interface between compressor portion and anchor portion whereby either the anchor trailing end or the compressor leading end fit within the other longitudinally a predetermined distance to allow axial rotation and longitudinal immobility.

Driving tools including a delivery tool and a compressor tool are provided for installing and then compressing the bones together, respectively. One embodiment of the delivery tool comprises a handle, adjoining shaft and loading portion, the loading portion being an extension of the shaft, the loading portion having at least one driving pattern that is complementary to at least one surface of a driven component, the loading portion also having a pin projecting forward from the driving pattern, the pin adapted to engage the cannula of both the coupler portion and the anchor portion. In an embodiment disclosed herein, the delivery tool loading portion comprises at least two driving patterns. The loading portion may further comprise a loading shaft and a blade, the loading shaft having a driving pattern that is complementary to a driven surface of the compressor portion, the blade having a driving pattern complementary to a driven surface of the coupler portion.

An embodiment of a method for fusing two adjacent bones and/or fragments to create a non-linear post-fusion orientation of the bones is provided comprising (a) providing a bone fusion apparatus comprising: (i) an anchor portion having an elongated body with screws threads on at least a portion of its exterior, the anchor having a leading tip and an end; (ii) a compressor portion having an elongated body with screw threads of the same pitch and diameter on at least a portion of its exterior; and (iii) a coupler having a first end adapted to rotatably engage the anchor in a first plane, the coupler also having a second end adapted to rotatably engage the compressor through axial rotation; (b) optionally preparing a channel in the adjacent bones through which the bone fusion apparatus is installed; (c) inserting the bone fusion apparatus through both bones while positioning the anchor-coupler interface at or near the natural joint location; (d) flexing the coupler-anchor interface to the desired degree of flexion; and (e) compressing the adjacent bones by reversing the rotation of the compressor portion sufficiently to impart the desired amount of compression while maintaining the desired alignment of the adjacent bones.

An embodiment of a method of maintaining thread synchronization of a bone fusion apparatus having a discontinuous thread is provided, the apparatus having a first screw thread on a leading component and a second screw thread on a trailing component, the two components being separated by a coupling non-threaded component, the separate screw threads having the same thread pitch, comprising providing at least two driving patterns in the trailing and non-threaded component to coordinate the separate screw threads with each other such that a single driving tool having the at least two complementary driving patterns will facilitate coordination of the screw threads by synchronized alignment and rotation of the trailing and non-threaded components.

BRIEF DESCRIPTION OF THE DRAWINGS

FIGS. 28-31 depict a linear two-part bone fusion embodiment.

FIGS. 1 and 2 are horizontal perspective computer-designed figures of the assembled DIP fusion device with compressor portion on the left and the anchor portion on the right;

FIG. 2 is the same picture but oriented pointing away from the viewer at approximately a 45 degree angle, thereby showing the interior of a portion of the compressor lumen.

FIGS. 3 and 4 are differing perspectives of exploded horizontal computer-designed figures of the three separate components of the DIP fusion device, e.g., the anchor portion on the left, the coupler immediately below, and the compressor portion immediately behind and to the right.

FIG. 4 is tilted downwards at a 45 degree angle to give a slightly different perspective.

FIGS. 5 and 6 are computer-aided horizontal perspective pictures of the anchor portion.

FIG. 7 is a top-down view of the anchor portion.

FIG. 8 is an end-down view of the anchor portion.

FIG. 9 is an inclined view of a computer-aided picture of the coupler portion of the apparatus.

FIG. 10 is a more inclined view of a computer-aided picture of the coupler portion of the apparatus so that the slot driving pattern is visible.

FIG. 11 is a view of the coupler along the plane of rotation of the coupler-anchor interface.

FIG. 12 is a similar view but rotated approximately 45 degrees to reveal additional features of the coupler.

FIG. 13 is a horizontal view of a computer-aided picture of the compressor portion.

FIG. 14 is a similar horizontal view but rotated so that a view down the lumen of the compressor is shown.

FIGS. 15 and 16 are compressor first end and compressor second end views, respectively, of the compressor lumen.

FIG. 17 is a horizontal view of a computer-aided picture of a cannulated delivery tool of the invention.

FIG. 18 is a close-up of the tip of the cannulated delivery tool of FIG. 17.

FIG. 19 is an extreme close-up of the tip of the cannulated delivery tool, with the tip angled towards the viewer.

FIG. 20 is a horizontal view of a computer-aided picture of a cannulated compressor tool of the invention.

FIG. 21 is a close-up view of the tip of the cannulated compressor tool of FIG. 20.

FIG. 22 is an extreme close-up view of the tip of the cannulated compressor tool, with the tip angled towards the viewer.

FIG. 23 is a close-up view of the tip of a non-cannulated delivery tool.

FIG. 24 is an extreme close-up view of the tip of the non-cannulated delivery tool of FIG. 23.

FIG. 25 is a cross-sectional isometric view of an exploded attachment assembly region.

FIGS. 26 AND 27 are cross-sectional isometric views of an assembled attachment assembly region, FIG. 26 in unlocked configuration, FIG. 27 in locked configuration.

FIG. 28 is an inclined isometric view of an exploded linear two-part bone fusion apparatus.

FIG. 30 is an inclined isometric view of an assembled linear two-part bone fusion apparatus.

FIGS. 32 and 33 are horizontal isometric views of a flexed or bent flexible bone fusion apparatus, FIG. 32 in full external view and FIG. 33 a cross-sectional view through the long axis.

DETAILED DESCRIPTION

1. Introduction

Figure 1:
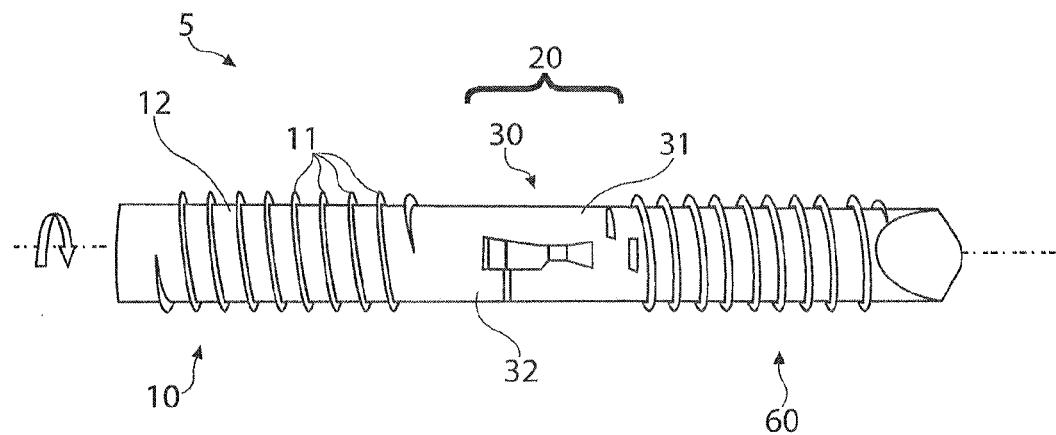
FIGS. 1-16, 32-33 depict a first embodiment of the DIP fusion apparatus.
Figure 2:
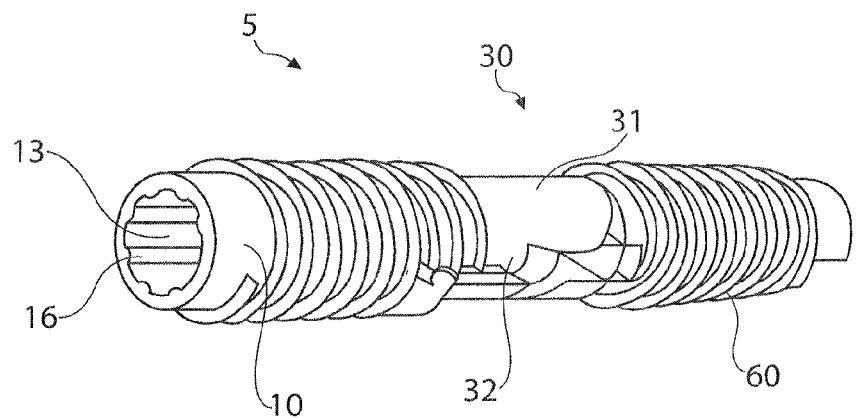

The various embodiments of the present invention provide a system, including methods, apparatus and kits for connecting bones and/or bone portions using a multi-part bone connector with one or more rotating joints. One problem in the art being addressed by the embodiments of the present invention is that of fusing two bones or fragments of a single bone that need to be fused in a non-linear manner, e.g., fusion of the distal and medial phalanges, in an aligned but slightly bent angle. Fusion of the distal interphalangeal ("DIP") joint to alleviate pain associated with Rheumatoid arthritis is a typical application. A first embodiment of a flexible bone fusion apparatus comprises an anchor portion having an elongated body with retaining elements, typically screw threads, on at least a portion of its exterior, the anchor having a leading tip and an end. The anchor is the leading part of the multi-part bone fusion apparatus and in a DIP application the anchor portion of the apparatus is driven into and resides permanently in the medullary cavity or canal of the medial phalange. The anchor works in combination with a second component called the compressor portion, which similarly has an elongated body with retaining elements that are typically screw threads of the same pitch and diameter as those of the anchor. If the device is installed through the fingertip, the compressor trails the anchor and is driven into and located in the distal phalange at the same time the anchor is driven into the medial phalange. In this first embodiment of the bone fusion apparatus and located between the anchor and compressor component parts is a flexible coupler, the coupler having an interface at each end for interfacing with the anchor and compressor, respectively. In one embodiment the coupler has a first end adapted to rotatably engage the anchor in a first plane with one degree of freedom. The first plane is defined by the two-component rotating attachment assembly shared between the coupler and the anchor. The coupler at its other end ("second end") engages the compressor which is adapted to rotatably engage the compressor through axial rotation. This is accomplished through a ridge-and-annular groove arrangement wherein the coupler shaft snaps into and is longitudinally retained by the compressor, yet they are free to rotate 360 degrees relative to each other around their mutual axis. This allows axial rotational freedom between the coupler and the compressor body which enables compression of the distal and medial phalanges when the compressor is rotated in reverse. "Axial rotation" is rotation about a transverse axis of the anchor and/or compressor portions as depicted by the rotating arrow in FIG. 1, which shows clockwise axial rotation about the axis of the assembled flexible bone fusion apparatus.

An advantage of this embodiment is that the anchor and compressor effectively share a continuous thread because the thread pitch and diameter on both are the same or very similar, and they are "clocked" or synchronized so that the threaded grooves cut into the medullary cavity of the distal phalange by the leading anchor threads are not disturbed by the trailing compressor screw threads. This allows for a simpler, one-step installation that does not require a second diameter channel drilled into the distal phalange to accommodate a larger compressor diameter. It also facilitates a less strenuous installation that enables the physician to have greater control when feeling for the "contact" point, or point at which the bones are backed into contact with each other.

A second advantage of this embodiment is that the anchor-coupler attachment region allows rotation in a single plane only, and then is locked in flexed position by reverse rotation of the compressor which pulls the anchor and compressor away from each other thereby locking the flexed orientation. This single-plane limitation is an advantage over prior art apparatus that allow for multiple degrees of freedom, thus allowing unwanted flex off the desired axis during the early healing phase.

2. Defined Terms

The terms "anchor," "anchor portion," "anchor element" or "anchor component" are used interchangeably to mean the leading component of a two- or three-component bone fusion apparatus described and taught herein. The second or trailing anchoring element is called by the interchangeable terms "compressor, "compressor portion," "compressor element" or "compressor component." The anchor portion and compressor portion both function as bone anchoring devices. Bone anchoring devices are well-known in general and can take many forms. The anchor components may include two or more discrete anchor elements that can engage bone to resist removal of each anchor element. Each anchor element may be unitary (one piece) or may be formed of two or more pieces, such as two or more pieces that are affixed to one another. The flexible bone fusion apparatus also may include one or more other discrete components, such as one or more discrete spacer components disposed between the anchor elements and/or one or more end components flanking the anchor elements adjacent one or both opposing ends of the connector.

The anchor elements may have any suitable size and shape. The anchor elements may be about the same length (the characteristic dimension measured parallel to the central axis) or different lengths. For example, the proximal (trailing) compressor element may be shorter or longer than the distal (leading) anchor element. The anchor elements may have about the same diameter or different diameters so long as the engaging thread pitch and diameters are substantially the same so that the initial thread groove cut by the leading anchor element is not disturbed by the following compressor. The diameter of each anchor element may be generally constant or may vary along the length of the anchor element. For example, the distal (and/or proximal) anchor element may taper distally, proximally, or both. Furthermore, the proximal and/or distal anchor element may have a distal tapered nose (threaded or nonthreaded) that enters bone first.

The flexible bone fusion apparatus may include a spacer region. The spacer region may have any suitable position(s) in the bone fusion apparatus and/or within an anchor element relative to a retention mechanism of the anchor element. For example, the spacer region may be disposed between a threaded region and a flexible joint of an anchor element. The spacer region may be unitary with an associated threaded region (or other retention structure) of an anchor element or may be formed by a distinct component joined fixedly (e.g., welded, bonded, or threadably coupled) or connected movably (e.g., coupled by a movable joint) to the threaded region (or other retention structure). The spacer region(s) may have any suitable length relative to the threaded region (or other retention structure) of an anchor element, including shorter, longer, or about the same length as the threaded region (or retention structure). Furthermore, the spacer region may have any suitable diameter or width relative to the threaded region (or retention structure) and/or protuberance, including a lesser (or greater) diameter or about the same diameter as that of the diameter of the threaded region. The spacer region may, for example, provide a nonthreaded region (and/or a non-anchoring portion of an anchor element(s)) to be disposed at the interface between bone members in which the flexible bone fusion apparatus is installed and/or may help define a range of bending motion of the flexible joint.

The bone fusion apparatus may define any suitable size and shape of lumen or cavity for any suitable purpose. The lumen may extend the entire length of the flexible bone fusion apparatus, such that the apparatus is cannulated, or may, for example, terminate before or after the lumen reaches the leading anchor element and before it reaches the leading end of the flexible bone fusion apparatus. The lumen may have a constant or varying cross-sectional geometry, which may be constant or vary within or compared between anchor elements. In some examples, the lumen may define a driver or delivery tool pattern in both anchor elements, so that a driver may extend through the trailing compressor element and into the leading anchor element, for concurrent engagement and rotation of both anchor elements. In some examples, the lumen may define a driver or delivery tool pattern in both the compressor element and an intervening flexing joint so that a driver may extend through the trailing compressor element and into the intermediate flexing joint, for concurrent engagement and rotation of both compressor and joint elements. In some examples, the lumen may narrow (or end) as it extends distally into the leading anchor element, to provide a shoulder for a tip of the driver to bear against, to facilitate driving the anchor into bone.

The terms "anchor-coupler interface" and "conical two-part single-plane interface" "attachment assembly 20" are used interchangeably to refer to the flexible joint assembly defined by the coupler-anchor interface of one of the present embodiments. The attachment assembly 20 is defined by the two attachment portions 21 and 22 shown in the figures. The word "flex" is used in the same manner as the term "bend" and is intended to convey a non-linear arrangement of the anchor and compressor portions.

Each anchor element may have any suitable retention mechanism. The anchor element may include a retention mechanism that is actuated by placement into bone and/or after placement into bone. The anchor elements of a flexible bone fusion apparatus may have the same type of retention mechanism (e.g., each having an external thread) or may have different types of retention mechanisms (e.g., one having an external thread and another having a nonthreaded engagement with bone).

A retention mechanism that is actuated by placement into bone may be defined by an anchor element that has a cross-sectional dimension (such as diameter) that is larger than the diameter of a hole into which the anchor element is placed. The anchor element thus may be disposed in a friction fit with bone (and/or may cut into bone) as it is placed into the bone. In some examples, the cross-sectional dimension may be defined in part by one or more projections that extend laterally from the body of the anchor element. Exemplary projections may include an external thread, one or more barbs, one or more circumferential ridges, one or more hooks, and/or the like. The projections may be biased (e.g., angled toward the trailing end of the anchor element), to facilitate insertion and to restrict removal. Alternatively, or in addition, the anchor element may have a cross-sectional dimension that increases toward an end (such as a trailing end) of the anchor element (e.g., a flared (e.g., frustoconical) anchor element). Anchor elements that engage bone and resist removal as they are placed into bone may be driven into bone rotationally (e.g., threaded into bone) and/or translationally (e.g., hammered into bone).

A retention mechanism that can be actuated in situ after placement of an anchor element into bone may be provided by expansion/deformation of the anchor element at a selected time after placement. The expansion/deformation may be any change in the structure of the anchor element that increases a cross-sectional dimension of the anchor element at one or more (or all) positions along the placement axis (e.g., the long axis) of the anchor element.

The flexible bone fusion apparatus may be configured as a bone screw having one or more anchor elements ("screw elements") with an external thread. The external thread may have any suitable thread structure. Each screw element may include a single thread (e.g., a continuous rib and/or furrow) or a plurality of threads. The plurality of threads may be disposed in discrete axial regions of the screw element (e.g., spaced proximal and distal threaded regions on the screw element) and/or may share the same axial region (e.g., to produce a multi-threaded configuration). The thread (or threaded region) of each screw element may extend over any suitable portion of the screw element's length, including at least substantially the entire length or less than about half the length, among others. The screw elements preferably have a thread of the same pitch to avoid creating more than one thread channel in the bone, thereby potentially weakening the bone or lessening the ability of the threads to be retained by the bone. The thread may have any other suitable features. For example, the thread (and thus the corresponding screw element) may have a constant or varying major and/or minor diameter within a screw element and/or between the screw elements.

In some embodiments of the flexible bone fusion apparatus, the screw elements, and particularly the leading screw element, may be configured to be self-drilling and/or self-tapping as the bone screw is advanced into bone. For example, a leading tip region of the leading anchor element may include a cutting structure(s) to drill bone, and/or a threaded region of either or both screw elements may include a tap region (such as one or more axial flutes, thread notches or tap faces among others) with a cutting edge(s) to tap bone.

The flexible coupler portion has two ends, one of which interfaces with the anchor and one of which interfaces with the compressor. There are two separate and independent interface designs disclosed herein: one is a snap-fit type interface which allows 360 degree axial rotation of one component relative to the other. The other interface is a two-part conical design which only allows rotation through a single plane from approximately 0 to 30 degrees in either direction. In the embodiment of Example 1, the design choice made was to locate the snap-fit interface at the compressor-coupler interface. Thus by default the two-part conical interface is located at the anchor-coupler interface.

The anchor elements of the flexible bone fusion apparatus may be connected by interfaces or joints suitable to provide the necessary motion. The joints may be movable between the anchor elements, operating by relative sliding motion (pivotal and/or translational) of apposed joint constituents. The joints may also rotate relative to each other. The joints may operate to restrict complete separation of the anchor elements in the absence of bone, while permitting relative rotational and/or translational motion of the anchor elements. The joints may be a composite connection formed collectively by two or more distinct movable joints.

The joints may permit any suitable relative motion. The joints may permit axial translational motion and/or lateral translational motion, or may substantially restrict either or both of these motions. The joints also or alternatively may permit rotational motion about the long axis and/or about one or more transverse axes of the flexible bone fusion apparatus. The rotational motion about the long axis may be unrestricted (allowing full turns) or restricted to less than a full rotation of the anchor elements. The rotational motion about the transverse axes may be determined by the structure of the rotational joint and/or joint constituents, for example, allowing an angular range of motion, about a selected transverse axis, of at least about 0 degrees and/or no more than about 10, 20, 40, or 60 degrees, among others.

The components may be formed of any suitable biocompatible and/or bioresorbable material(s). Exemplary biocompatible materials include (1) metals (for example, titanium or titanium alloys; alloys with cobalt and chromium (cobalt-chrome); stainless steel; etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; (5) bioresorbable (bioabsorbable) materials or polymers (for example, polymers of alpha-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-beta-hydroxybutyrate, poly-beta-hydroxypropionate, poly-delta-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone tissue (e.g., bone powder and/or bone fragments); and/or the like. In some examples, these materials may form the body of an anchor element and/or a coating thereon. The anchor component may be formed of the same material(s) or different materials. Exemplary configurations with different materials may include a coupler formed of metal with leading anchor element formed of a titanium alloy and a compressor made of a polymer; a leading anchor element formed of cobalt-chrome, a coupler formed of metal and a trailing compressor element formed of a bioresorbable material, among others. The choice of materials is generally within the skill of a person having ordinary skill in the art of implantable medical devices.

The flexible bone fusion apparatus of the present teachings may be fabricated by any suitable process(es). For example, the anchor and coupler elements of the apparatus may be formed separately and then connected to one another.

Each anchor element may be formed by any suitable process(es). Exemplary processes include EDM, molding, machining, casting, forming, crimping, milling, and/or the like. Threads or other retention structure on the anchor elements may be formed at the same time as and/or after formation of other portions of the anchor elements.

The anchor elements and coupler may be connected by any suitable process that allows for the necessary movement after connection. Exemplary processes include snap-fitting the coupler into the lumen of the compressor element, to form a rotatable joint. The compressor lumen may have a mouth that is larger than the width of the coupler, so that the coupler, once it is forced past the mouth and engages the annular grooves within the coupler, remains trapped in the lumen. Other exemplary processes include disposing a coupler in a lumen having a lip, and then crimping or otherwise deforming the lip so that the coupler is retained in the lumen.

The flexible bone fusion apparatus may be installed by any suitable methods. Exemplary steps that may be performed are listed below. These steps may be performed in any suitable order, in any suitable combination, and any suitable number of times.

At least two bone members may be selected. The bone members may correspond to different bones or distinct fragments of the same bone, among others. The bone members may be adjacent one another naturally or may be moved so that they are adjacent one another. The bone members may have sustained or be associated with any suitable injury. For example, the bone members may result from an injury to bone (such as a fracture and/or an osteotomy, among others) or may be adjacent and/or connected to injured soft/connective tissue (e.g., ligament, tendon, and/or muscle, among others). In some examples, the bone members may be bones that articulate with one another through an anatomical joint. Any suitable anatomical joints may be selected, including the scapholunate joint, the acromioclavicular joint, DIP joint, etc. Any suitable adjacent bones may be selected, including bones of the hand (e.g. phalanges), wrist (e.g., carpal bones), arm, foot (e.g. metatarsals), ankle, leg, shoulder, etc.

A bone fusion apparatus may be selected. The bone fusion apparatus may have any combination of the features described elsewhere in the present disclosure including having a flexible joint or a non-flexible, linear configuration. Furthermore, the bone fusion apparatus may have a size (e.g., length and width) selected according to the size of the bone members into which the bone fusion apparatus is to be placed (e.g., a narrower and/or shorter bone fusion apparatus for smaller bone members and a wider and/or longer bone fusion apparatus for larger bone members).

A distinct advantage of a flexible bone fusion apparatus is that it may fuse adjacent bones together at the location of a previously flexible joint, yet replicate some degree of natural curvature even if the joint itself is now permanently immobile. The flexible bone fusion apparatus may be installed into the bone members. In particular, a leading anchor element of the flexible bone fusion apparatus may be advanced first through a more proximal (closer and/or more accessible) of the bone members and then into a more distal (farther and/or less accessible) of the bone members. A trailing anchor (compressor) element of the flexible bone fusion apparatus may follow the leading anchor element into the proximal bone member. The anchor elements may be positioned such that each anchor element is at least mostly (or completely) disposed within a different one of the bone members. A rotatable joint of the apparatus may be disposed generally between the bone members, such as overlapping with and/or proximate to an anatomical joint through which the bone members articulate. In some examples, the flexible bone fusion apparatus may include a nonthreaded region disposed between spaced threaded regions. Each threaded region may be placed at least mostly or completely in a different bone member, with the nonthreaded region extending between the bone members. In some examples, a retention mechanism may be actuated for one or both anchor elements to restrict removal of the anchor element(s) from bone, after one or both anchor elements have been placed into the bone members. In some examples, one of the anchor elements may be disposed in threaded engagement with bone during placement into bone and the other anchor element may be restricted from removal by actuation of a retention mechanism after the other anchor element is disposed in bone.

The flexible bone fusion apparatus may be placed into a pre-formed hole in the bone members. The hole may be formed, for example, by drilling through the proximal bone member and into the distal bone member (or vice versa). In some examples, the hole may be formed by drilling over a wire placed into the bone members, to define a guide path along which a drill and the flexible bone fusion apparatus travel. Accordingly, the drill and/or flexible bone fusion apparatus may be cannulated so that each can slide along the wire. Alternatively, the flexible bone fusion apparatus (and particularly a flexible bone screw) may be self-drilling so that it forms and/or widens its own hole as it advances into bone.

The flexible bone fusion apparatus may be left in place permanently or may be removed at a later time. Removal of the flexible bone fusion apparatus may take place at any suitable time. Exemplary times include at a predefined time or after a predefined amount of healing. In some examples, the flexible bone fusion apparatus (and/or an anchor element thereof) may be bioresorbable, so that the flexible bone fusion apparatus (and/or an anchor element thereof is broken down by the body over time.

3. Examples

The following examples are illustrations of selected embodiments of the inventions discussed herein, and should not be applied so as to limit the appended claims in any manner.

Example 1

Cannulated Flexible Three-Part DIP Fusion Apparatus

FIGS. 1-16, 32-33 disclose a first embodiment of the invention which may or may not be designed to be installed over a K-wire. The flexible bone fusion apparatus 5 of FIG. 1 comprises three main components, a compressor portion 10, coupler portion 30 and anchor portion 60. The coupler portion imparts overall flexibility to the design and allows the bone fusion apparatus to flex in a single plane at a DIP joint to emulate a natural curvature of the joint (e.g., finger or toe) post-fusion. FIG. 1 depicts all three components together in their unlocked assembled arrangement. When installing the device in bones such as either the finger or toe a cannulated delivery tool 100 (FIGS. 17-19) is inserted into the end of the assembled flexible bone fusion device 5. The delivery tool resembles a screwdriver in that it has a handle and shaft, but this tool is specially adapted to engage the compressor lumen of the bone fusion device through seven compressor grooves 107 that mate with seven compressor lumen ridges 16 inside the lumen of the compressor. The cannulated delivery tool is described in more detail later and is mentioned here only to explain the utility of the compressor lumen ridges 16.

Figure 3:
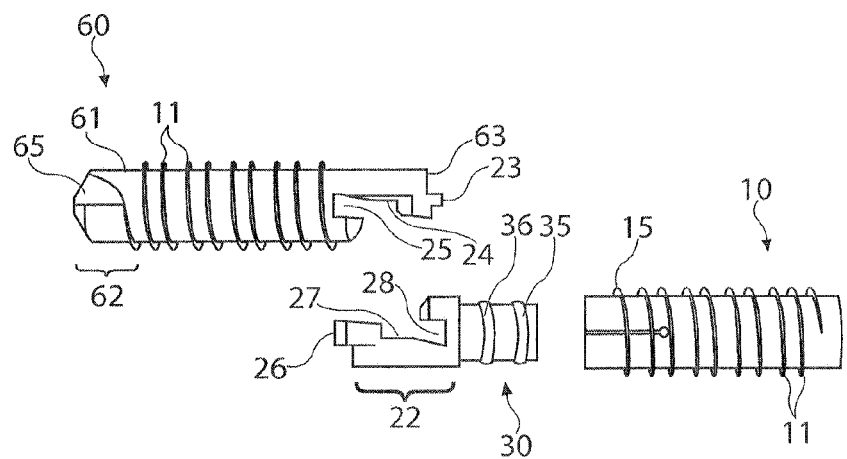
Figure 4:
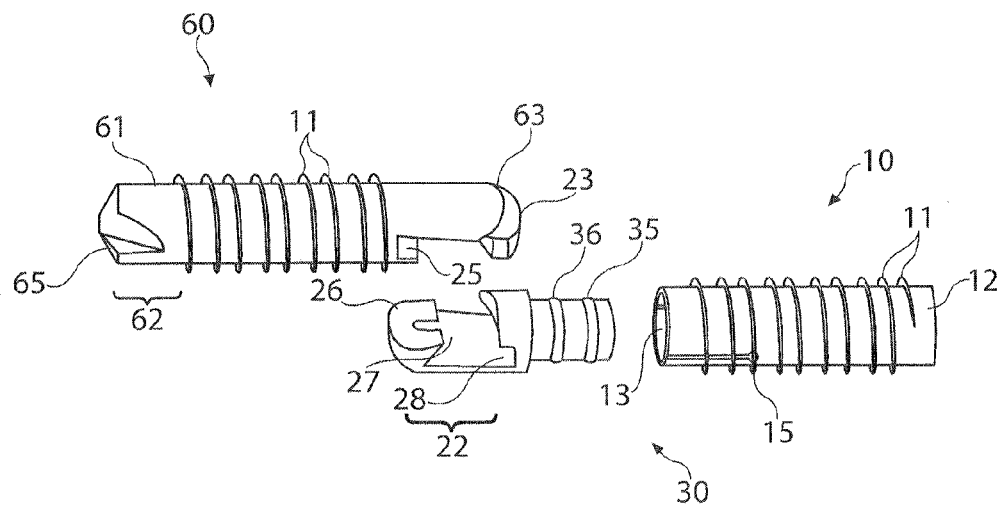

FIGS. 3 and 4 show an exploded horizontal perspective figure of the bone fusion device. Anchor portion 60 has an anchor body 61 that is made from any material suitable for medical implantation such as stainless steel, titanium, or a biologically compatible polymer. The main requirements are that the material be strong yet light, be sanitizable, and withstand the usual rigors of installation. A preferred embodiment is made from titanium. The embodiments shown throughout this description are made via Electric Discharge Machining, (EDM) a technique well-known in the machining arts, lathe cutting, grinding, abrasion and polishing. The dimensions of the anchor body are from about 10 mm to about 40 mm in length, and a diameter from about 2 mm to about 5 mm. Disposed upon at least a portion of the anchor body 61 are screw threads 11. In the first embodiment the threads are of a uniform diameter and pitch (distance between adjacent threads), although the leading tip of the anchor may also utilize a screw thread having a smaller leading diameter to initially engage the bone. A typical thread diameter ranges from about 2.5 mm to about 6 mm. Thread diameters will of course vary depending upon the desired application.

Anchor portion 60 has a leading tip 62 that has a tap edge 65 useful for cutting through bone. The tap edge 65 is cut from the conical tip and body such that when the tip is rotated in contact with bone the cutting surface will engage the bone and carve the bone away at the leading edge. The conical portions of the leading tip 62 have utility for guiding the apparatus into the medullary canal of the bone, if the application is such that the area of bone being targeted for repair has a canal. In some applications a channel through the bone is drilled to act as a guide for the bone fusion apparatus and so the tap edge 65 may not come into contact with bone during the installation process unless the channel is too narrow or short.

Figure 5:
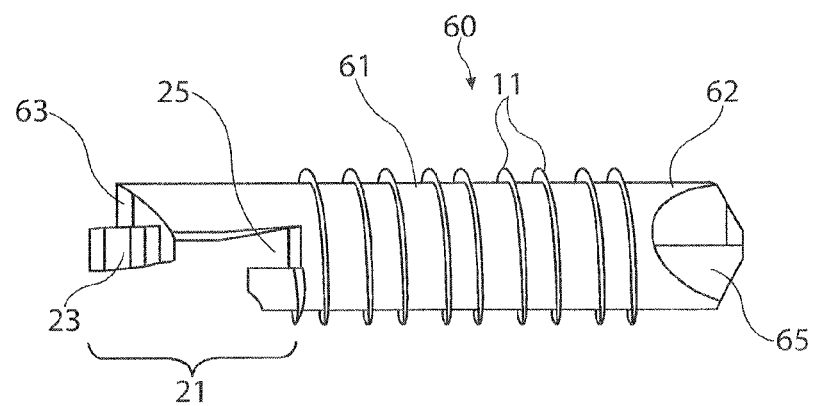
Figure 6:
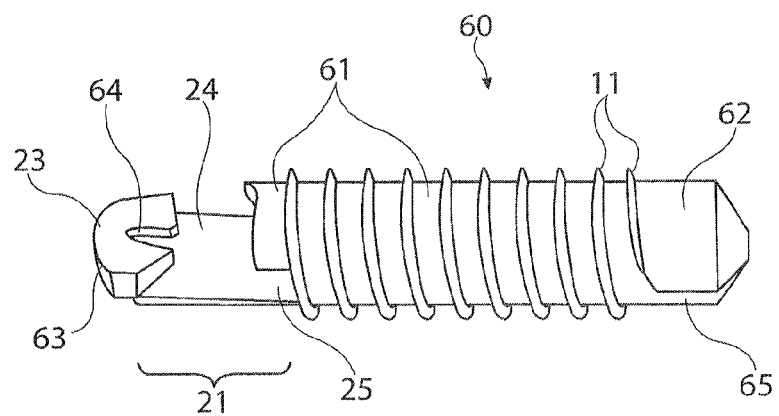
Figure 25:
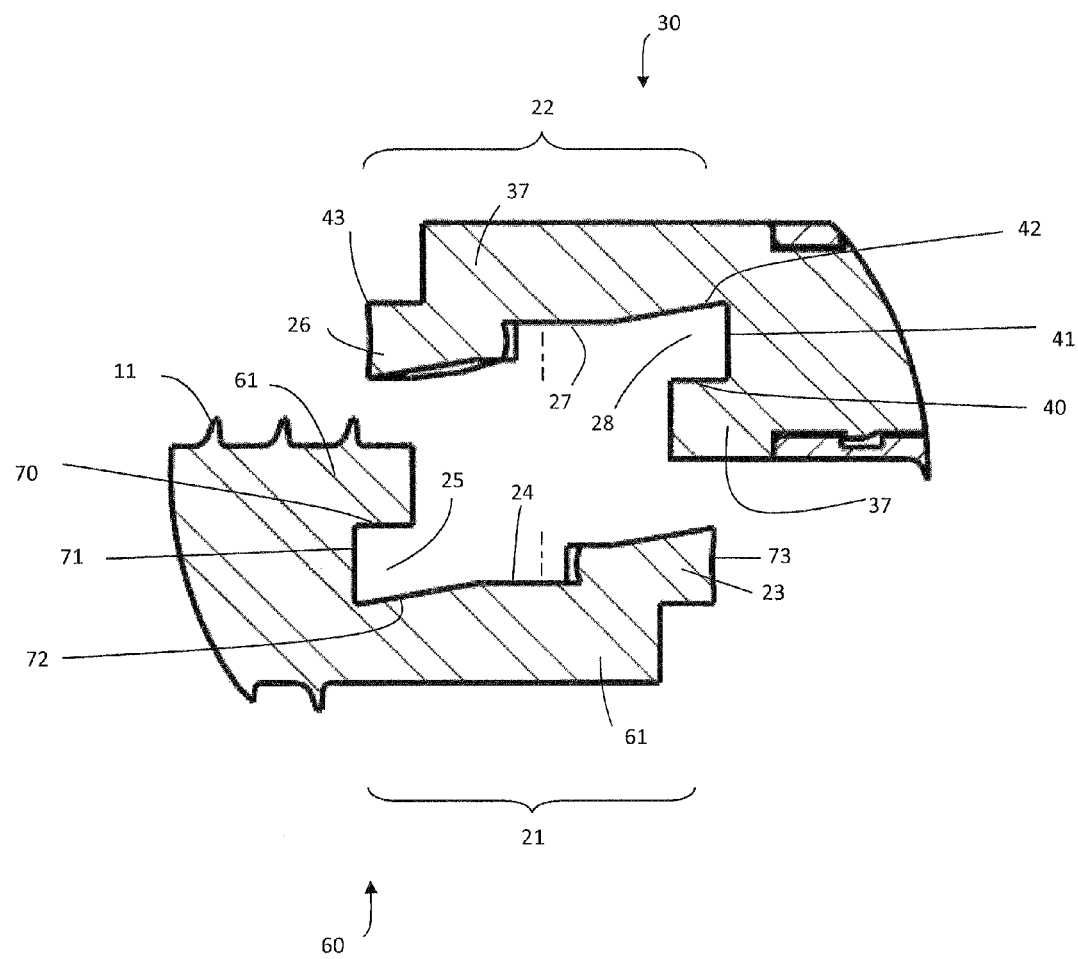
FIGS. 25-27 depict a cross-section of the attachment assembly.

The end of the anchor portion 60 that engages the coupler 30 is the anchor attachment portion 21, seen best in FIGS. 5-6 and FIG. 25. Anchor attachment portion 21 has three main features for facilitating rotating attachment to coupler attachment portion 22 of coupler 30. The first feature is the anchor locking wedge 23. Anchor locking wedge 23 is an irregularly-shaped element that fits into annular groove 28 of coupler attachment portion 22. It has three main functions: to hold the top of the anchor attachment portion 21 within the coupler annular groove 28; when unlocked, to facilitate rotation in a single plane; and when installed to lock the angled configuration of the bone fusion apparatus in place. Anchor locking wedge 23 has a greater thickness at the anchor locking wedge edge 73 that engages with the opposing coupler groove bottom 41, as shown in FIG. 25, and so it forms a wedge-shape that is retained in coupler annular groove 28 due to the restrictive dimensions of the coupler groove. (Coupler locking wedge edge 43 is similarly designed to be thicker at its periphery than its internal margin thereby to be retained in complementary anchor annular groove 25.)

The second feature of anchor attachment portion 21 is the anchor annular groove 25, which like the coupler annular groove 28 is designed to accept and retain the locking wedge from the complementary attachment portion. Anchor annular groove 25 is defined by the anchor body 61 on one side, specifically the anchor groove inner wall 70, the anchor groove bottom 71, and the lower portion of the anchor axial face 24 on the side opposing the anchor body 61, the anchor groove semi-circular conical face 72. It will be noted that anchor groove semi-circular conical face 72 is not parallel to its opposing wall, but declines at approximately a 10 degree angle to provide a means for creating a friction face when the coupler and anchor are pulled apart. The 10 degree angled surface defines a partial cone in three dimensions, and the surface of the anchor groove semi-circular conical face 72 is therefore termed "conical," although the apex of the cone, if present, would inhabit the empty space immediately above the axial face 24. It should be noted that other surfaces may also serve the function, including a spherical surface.

The third feature of anchor attachment portion 21 is the anchor axial face 24. The anchor axial face is a flat area that defines the rotational axis about which both attachment portions rotate, the center of the axis denoted by the dashed lines in FIGS. 25-27. The area is flat so that the inner portions of the locking wedges may slip without constraint towards the center thereby allowing the locking function. The anchor groove semi-circular conical face 72 feature functions to center the opposing faces during rotation.

Complementary coupler attachment portion 22 has the same features with the same overall function and design features as the anchor attachment portion, but the features are reversed to complement or fit within the anchor attachment portion features. In this way they function together as a two-part interface to rotate about the single plane defined by the semi-circular conical faces located at the center of the attachment assembly 20. As previously mentioned, the anchor locking wedge 23 fits within the coupler annular groove 28 because the groove is machined to have a similar shape for receiving and holding the wedge, but in a manner that allows some amount of "slip" along the longitudinal axis of the flexible bone fusion device.

Coupler attachment portion 22 has three main features for facilitating rotating attachment to anchor attachment portion 21 of anchor 60. The first feature is the coupler locking wedge 26. Coupler locking wedge 26 is an irregularly-shaped element that fits into anchor annular groove 25 of anchor attachment portion 21. It has three main functions: to hold the top of the coupler attachment portion 22 within the anchor annular groove 25; when unlocked, to facilitate rotation in a single plane; and when installed to lock the angled configuration of the bone fusion apparatus in place. Coupler locking wedge 26 has a greater thickness at the edge 43 that engages with the opposing anchor groove bottom 71, as shown in FIG. 25, and so it forms a wedge-shape that is retained in anchor annular groove 25 due to the restrictive dimensions of the anchor groove.

The second feature of coupler attachment portion 22 is the coupler annular groove 28, which like the anchor annular groove 25 is designed to accept and retain the locking wedge from the complementary attachment portion. Coupler annular groove 28 is defined by the coupler body 37 on one side, specifically the coupler groove inner wall 40, the coupler groove bottom 41, and the lower portion of the coupler axial face 27 on the side opposing the coupler body 37, the coupler groove semi-circular conical face 42. It will be noted that coupler groove semi-circular conical face 42 is not parallel to its opposing wall, but inclines at approximately a 10 degree angle to provide a means for creating a friction face when the coupler and anchor are pulled apart. The 10 degree angled surface defines a partial cone in three dimensions, and the surface of the coupler groove semi-circular conical face 42 is therefore termed "conical," although the apex of the cone, if present, would inhabit the empty space immediately above the axial face 27. It should be noted that other surfaces may also serve the function, including a spherical surface.

The third feature of coupler attachment portion 22 is the coupler axial face 27. Coupler axial face 27 is a flat area that defines the rotational axis about which both attachment portions rotate, the center of the axis denoted by the dashed lines in FIGS. 25-27. The area is flat so that the inner portions of the locking wedges may slip without constraint towards the center thereby allowing the locking function. The coupler groove semi-circular conical face 42 feature functions to center the opposing faces during rotation.

After manufacture of the compressor portion and coupler portion the two parts may be assembled by hand. This involves aligning the anchor attachment 21 and coupler attachment 22 portions so that they face each other as in FIGS. 3-4 and/or 25-27 and rotating them to approximately 69 degrees off-axis. Since this embodiment has been designed to assemble and function at this angle, they will fit into each other's complementary features. Rotation to 0 degrees will assemble them for further post-assembly steps such as cleaning, sterilization and packaging.

Figure 26:
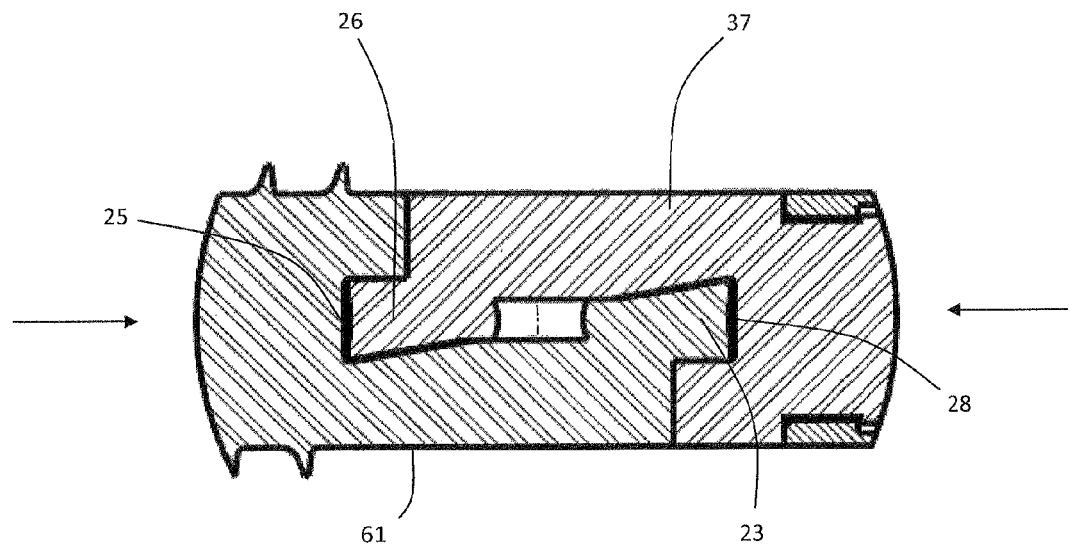
Figure 27:
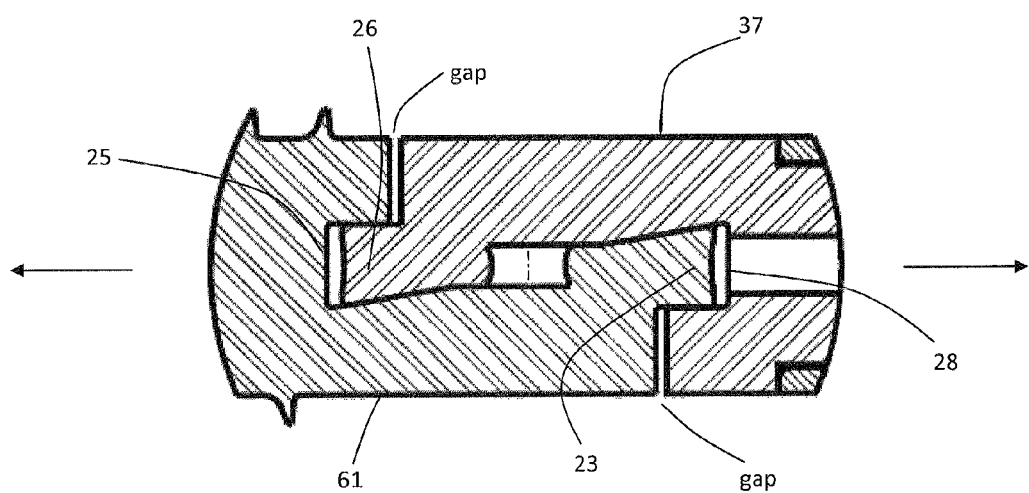

With reference to FIGS. 26-27, FIG. 27 is a cross-section of the assembled DIP fusion device in the locked configuration. There are gaps at the peripheries between the coupler body 37 and the anchor body 61, indicating that the two components have been pulled apart along their longitudinal axis (in the direction of the arrows), thus driving the upper locking wedge portions 23, 26 of both devices into their respective annular grooves 28, 25. In the configuration shown in FIG. 27 friction between the interlocking wedges and mating groove faces constrains further rotational motion after they have been pulled apart in this manner. FIG. 26 shows the same components in their unlocked configuration where the components have been pushed together (in the direction of the arrows) thereby freeing the wedges from the grip of the grooves and allowing rotational motion in the plane defined by the axial faces 24 and 27. Thus both the anchor annular groove 25 and the coupler annular groove 28 have groove depths that exceed the length of the corresponding locking wedges 26, 23 enough to facilitate the locking function. In this embodiment, the depths are typically from about 0.75 mm to about 1.5 mm.

Anchor portion 60 also has an anchor lumen 64 which follows the longitudinal axis of the anchor from one end through the other. The lumen is not shown in FIGS. 25-27 for purposes of clarity. The lumen (or cannula) is useful for facilitating installation over a k-wire, or for allowing the alignment pin 105 (see FIGS. 23-24) on the tip of the delivery tool 100 to engage and straighten the three elements during installation of the bone fusion apparatus.

Now with reference to FIGS. 9-12, an embodiment of coupler portion 30 includes two main areas of interest, the uppermost coupler attachment portion 22 and the lower half which comprises an axial interface for rotational attachment to the compressor portion 10. As previously described with reference to the anchor attachment portion 21, the three main features for facilitating rotating attachment to anchor attachment portion 21 include a coupler locking wedge 26, a coupler axial face 27 and a coupler annular groove 28. Since the coupler attachment portions have been designed to be complementary to each other, the features have the same general design and function as the features of the anchor attachment portion and are only briefly mentioned. In addition to the three elements of the coupler attachment portion 22, coupler 30 has a coupler first end 31 which is where the coupler locking wedge 26 is located. There is also a coupler second end 32, located at the lower half of the coupler in FIGS. 9-12. The coupler second end comprises a coupler body 37 roughly cylindrical in shape with a lumen 33 running along its axial core, similar to the lumen of the anchor. Coupler body 37 has an external diameter which is sized to fit within compressor portion 10. In this embodiment, the external diameter of the coupler is 2.7 mm. The coupler body 37 has at least one annular ridge 35 disposed upon its surface for engaging with mating compressor annular groove 14 in compressor 10 (see FIG. 14). In a preferred embodiment coupler body 37 has at least two sets of coupler annular ridges 35 and 36 spaced some distance apart longitudinally for engaging in snap-in fashion with the at least two annular grooves 14 and 17 of compressor lumen 13. Coupler annular ridges 35 and 36 do not have to be continuous, but can be discontinuous shoulder-type ridges as shown in FIGS. 9-12.

Figures 9, 10:
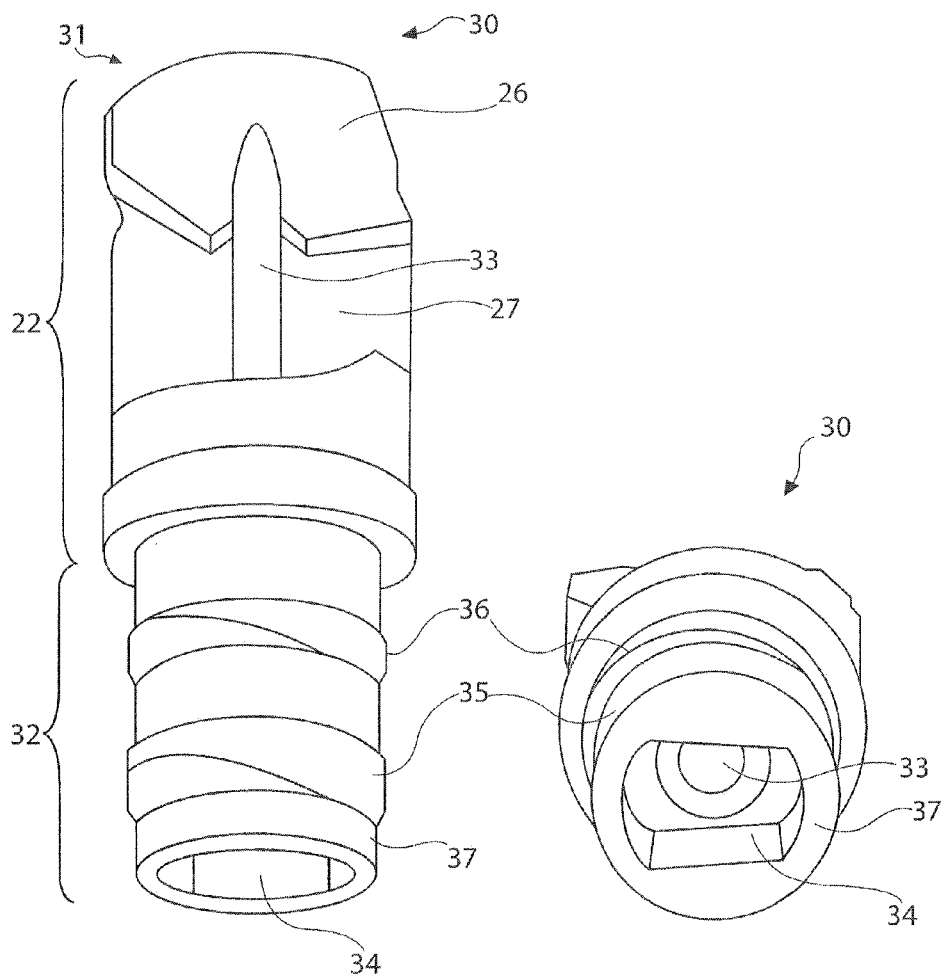
Figures 11, 12:
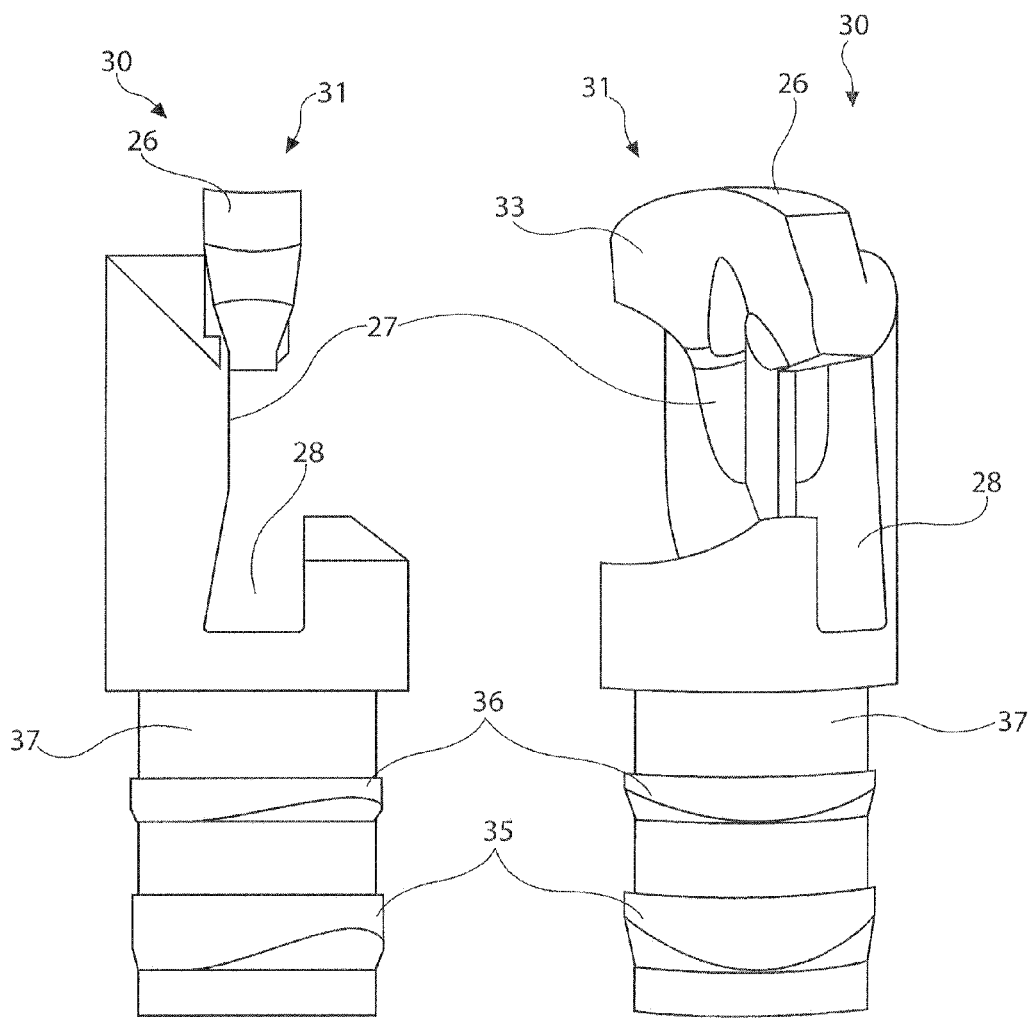
Figure 13:
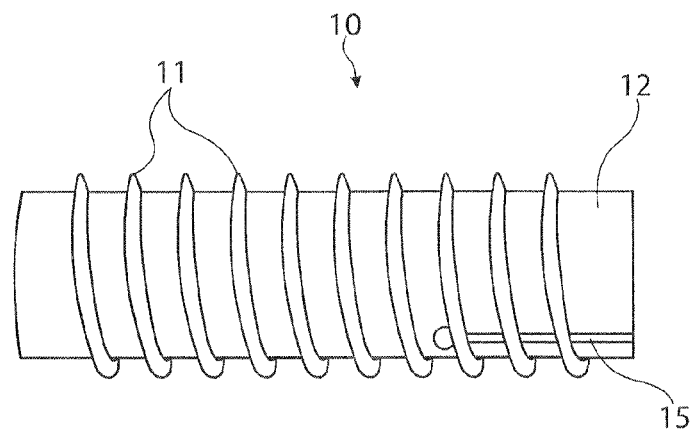

With reference to FIG. 9 there is also shown a keyed coupler slot 34, shaped in the general form of a wedge rounded at both ends, that engages with the complementary delivery tool blade 108 (see FIGS. 17-19, 23-24). The function of coupler slot 34 and blade 108 is to synchronize the axial alignment of the compressor, anchor and coupler so that upon installation the threads of the compressor and anchor are clocked, i.e., in external alignment so that together the threads cut one continuous channel, and also to ensure that the external alignment marks will correctly identify the top dead center of the attachment assembly 20. The slot-and-blade combination is "keyed" in that there is a single orientation of the blade that will fit the slot. It should be understood that the slot-and-blade choice of synchronization is merely a matter of design choice, and other equally functional combinations of a keyed depression (slot) and a complementary blade may be chosen without departing from the spirit of the invention. A person having ordinary skill in the machining art will be able to recognize and implement numerous designs for the keyed blade-and-slot combination, including a modified Phillips pattern, a modified TORX bit pattern, etc.

Also with reference to FIG. 10, a countersunk and drilled shaft or coupler lumen 33 abuts the coupler slot 34. As previously described in reference to the anchor lumen 64, the coupler lumen 33 similarly is adapted to receive the Delivery Tool alignment pin 105. Coupler lumen 33 extends completely through the axis of coupler 30, including the coupler body 37, the coupler annular groove 28 and the coupler locking wedge 26.

Figure 14:
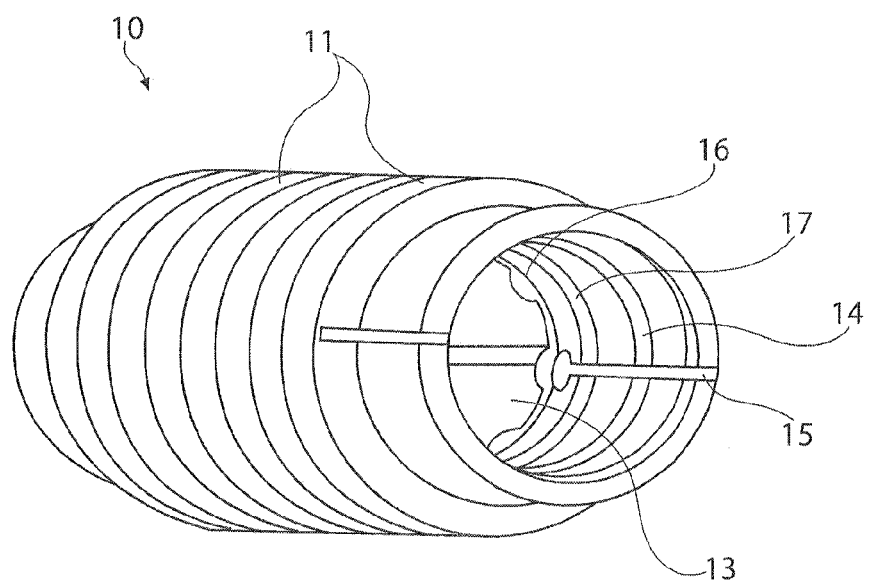
Figure 15:
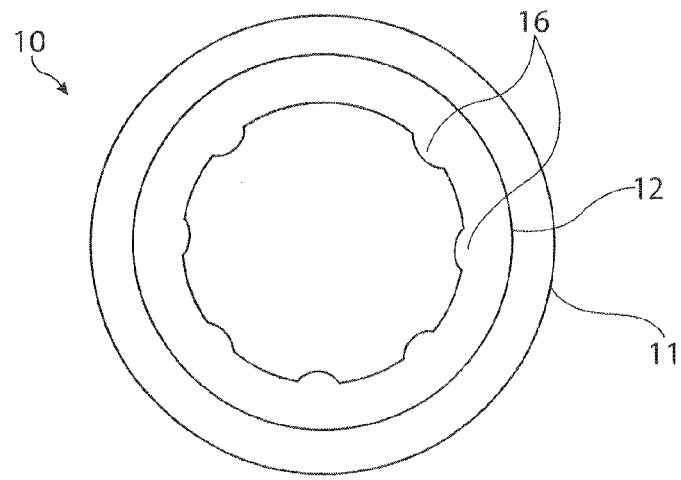
Figure 16:
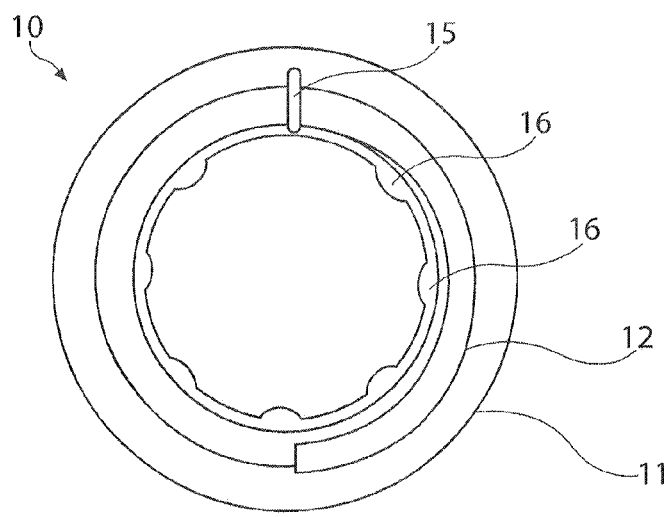

With reference to FIGS. 13-16, an embodiment of compressor portion 10 is shown. Compressor portion 10 is adapted to engage with coupler 30 at one end, and also to engage with delivery and compressor tools through the compressor lumen 13. In this embodiment, compressor portion 10 is a single piece having a body 12 with retaining means such as threads 11 disposed on its external surface. The threads have the same pitch and diameter as the threads of the anchor portion so as to synchronize with the anchor threads. Compressor portion 10 also has a compressor lumen 13 having compressor lumen ridges 16 running lengthwise (or longitudinally) that engage the compressor grooves 107 on Delivery and Compressor Tools 100, 110, respectively. With reference to FIGS. 15 and 16 there is seen the ridges in cross-sectional perspective. FIG. 14 shows 7 distinct compressor lumen ridges 16 starting at the end of the compressor portion 10 and continuing to the region of the compressor annular grooves 14, 17. The length of the ridges should be sufficient to facilitate an adequate grasp of the compressor as the bone fusion assembly is being installed and so is a design choice. In a preferred embodiment the ridges range from about 5 mm to about 10 mm in length. The seven ridges are spaced octagonally, but the eighth is left out creating a "flat spot" (i.e an absence of a ridge). There is a matching flat spot on exterior drive shafts of the delivery and compressor tools, as seen best in FIGS. 19 and 22. This allows keying of the axial orientation between the tools and the compressor.

For a person having ordinary skill in the art, the detailed implementation of a snap-fit interface is well within his or her skill level. In this embodiment compressor portion 10 has one or more slots 15 cut into and through the body to allow for some radial expansion of the body as the coupler is being press-fit into it. Compressor portion 10 has internal compressor annular grooves 14, 17 cut into the lumen surface to accommodate the coupler annular ridges 35, 36. When the coupler second end (facing the compressor) is pressed into the internal diameter of the compressor, the compressor body will expand slightly and then as the ridges reach the grooves the ridges will snap down into the grooves and stop there. The fit of the grooves and ridges is such that axial rotation is allowed, that is, the diameter at the base of the grooves is close to the external diameter of the ridges. In a preferred embodiment this diameter is about 2.5 mm. In this embodiment, the function of the snap-fit interface in the assembled bone fusion apparatus is to allow free rotation of the compressor portion about the coupler portion. In this embodiment the coupler will be fixed and the compressor will rotate axially to adjust the amount of distance between the two bones or bone fragments. The free rotation at the coupler-compressor interface facilitates compression by insertion of the compressor tool into the compressor lumen, then rotating the compressor portion 10 counterclockwise until the bones contact each other.

Figure 17:
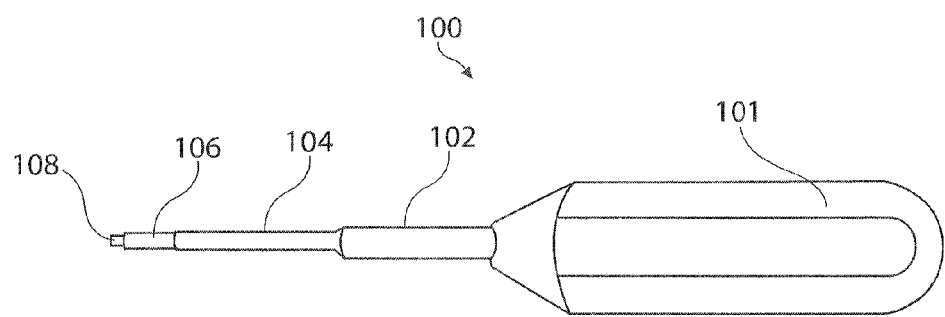
FIGS. 17-19 depict an embodiment of the delivery tool.
Figure 18:
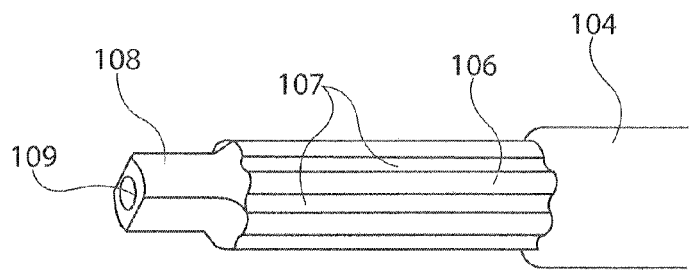
Figure 19:
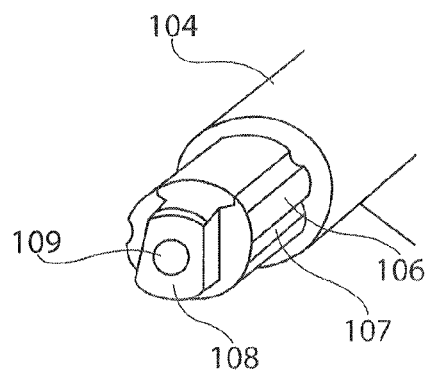

FIGS. 17-19 are computer-generated pictures of a cannulated delivery tool 100. Delivery tool 100 is "keyed" or designed with an external surface having one or more driving patterns complementary to that of the lumen of compressor 10. A "driving pattern" is a pattern of grooves, splines, blades or similar machined surfaces that mate with a complementary surface. An example is a TORX® drive, which is a machined shaft having a series of longitudinal grooves that engage a TORX screw or other fitting having a six-sided star-shaped pattern that is designed to accept a TORX driver and nothing else. Other drive patterns include a spline, double hexagonal, hexagonal, tri-wing, triple square, etc. This embodiment comprises a conventional handle 101 adapted to fit the hand of an adult. The handle is attached to a shaft comprising shaft 102, delivery shaft 104, and a loading portion comprising a loading shaft 106 and a blade 108. Shaft 102 and delivery shaft 104 are of conventional design and are similar to the shaft of a screwdriver. Loading shaft 106 is designed to fit within compressor lumen 13 and complement the compressor lumen ridges 16, of which there are seven arranged in octagonal fashion as previously described. Loading shaft 106 has compressor grooves 107 machined into the surface of loading shaft 106 and accommodate the compressor lumen ridges 16 when the delivery tool is inserted into the compressor portion. The flat spot resulting from the "missing" eighth groove is best seen in FIG. 19 as the rounded top portion of loading shaft 106 that is between two compressor grooves 107.

Because both the compressor and coupler have surfaces that mate with the delivery tool, the tool is able to engage both the compressor portion and the coupler portion simultaneously yet through separately keyed surfaces. This allows the delivery tool to drive all three components in synchrony since the coupler is also attached to the anchor portion. In this embodiment delivery tool blade 108 (FIGS. 18-19) is shaped to fit into the coupler slot 34 (FIG. 10) of coupler portion 30 in complementary fashion. As can be seen in FIG. 19, blade 108 is generally wedge-shaped in cross-section and has four sides, two of which are opposing rounded sides, the other two being opposed flat sides. In this embodiment the opposing straight sides are not parallel. The blade-and-slot complementary combination are not unique and can assume any complementary configuration to enable the keying function.

Figure 23:
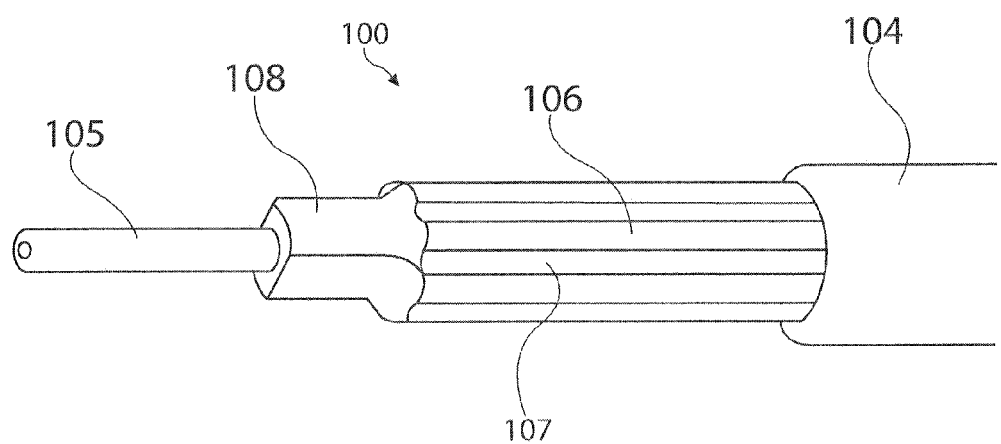
FIGS. 23-24 depict a second embodiment of the compressor tool.
Figure 24:
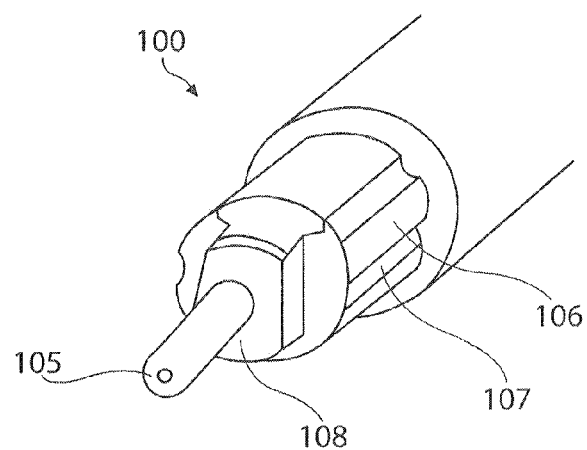

To hold the coupler and anchor in straight alignment during installation without a K-wire an alignment pin 105 is provided. With reference to FIGS. 23-24, a delivery tool 100 with an alignment pin 105 is shown. In this embodiment the portion of the lumen that accommodates the delivery tool alignment pin 105 necessarily is size-adapted so that the pin fits within the diameter of the lumen and is able to accomplish the alignment function. The length of the pin must be sufficient to intersect both the coupler locking wedge 26 and the anchor locking wedge 23, and in this embodiment this diameter is typically from about 0.7 mm to about 1 mm.

Figure 20:
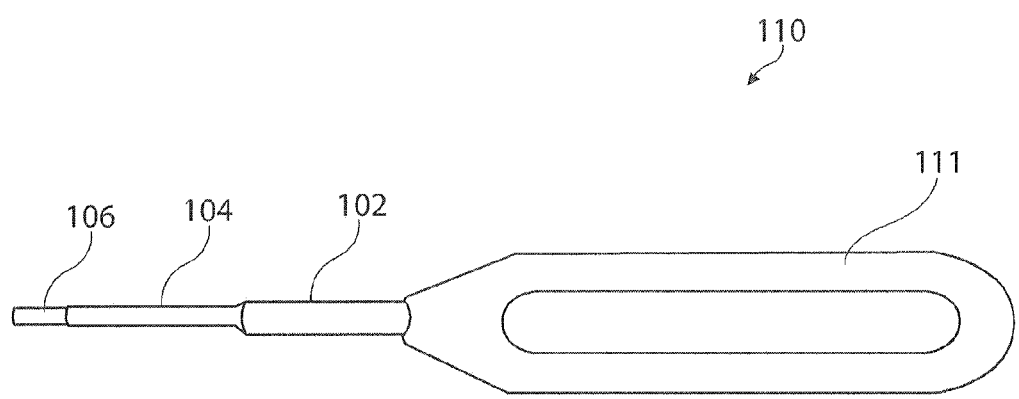
FIGS. 20-22 depict an embodiment of the compressor tool.
Figure 21:
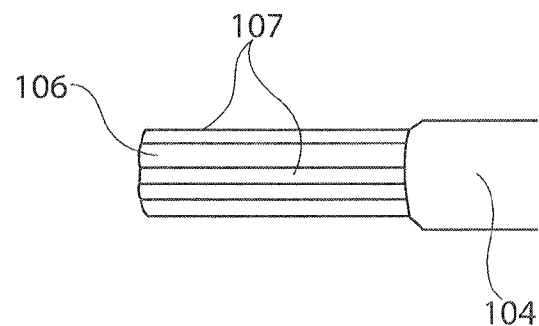
Figure 22:
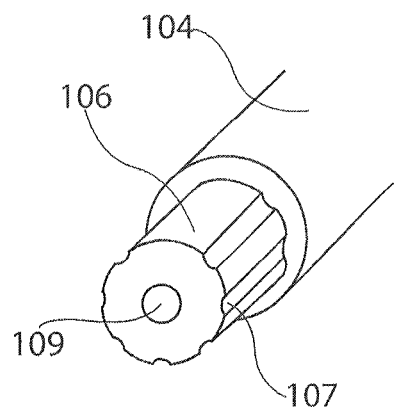

After the fusion apparatus has been driven into position in the medial and distal phalanges, compression of the bones may be desired. To compress the bones a separate tool called a "Compressor Tool" is used. Cannulated compressor tool 110 is best seen in FIGS. 20-22 and comprises the same design as delivery tool 100 with the exception of the absence of the blade 108. The compressor tool 110 may have all of the same design features as the delivery tool, but the blade portion is absent so that it will no longer engage the coupler 30, but it will engage the compressor 10 so that the compressor may be rotated separate and apart from the coupler. The design of the axial interface also allows for independent axial rotation of the compressor and coupler. In an alternate embodiment of the compressor tool, the handle may be differently dimensioned to distinguish it from the delivery tool by feel.

In one embodiment compressor tool 110 may have a lumen or delivery tool lumen 109 running through its center. In the fully assembled flexible bone fusion apparatus 5 the cannula may be useful when installing the bone fusion apparatus over a K-wire, as is well-known in the art. The cannula may extend from the leading tip 62 of the anchor portion 60 all the way through the coupler portion 30, compressor portion 10 and also through the delivery tool 100. Alternatively, a K-wire may not be used with this apparatus, in which case the delivery tool without a cannula but with an alignment pin may be used, as shown in FIGS. 23-24. In this embodiment, the delivery tool is identical to the previous embodiment except that it has no cannula, but it has the alignment pin shown and previously described. The DIP fusion apparatus does not vary if a K-wire is used or not due to the fact that the apparatus already has a lumen traversing its length.

Figure 32:
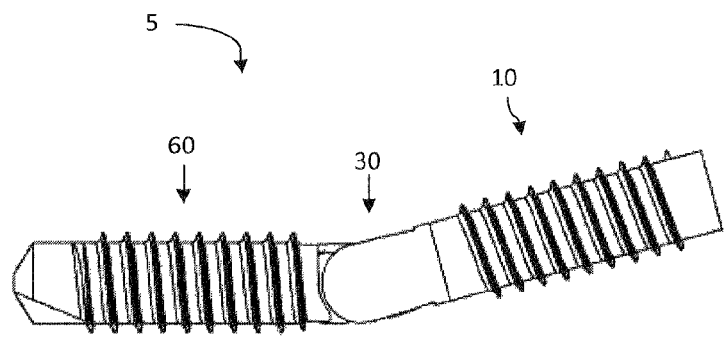
Figure 33:
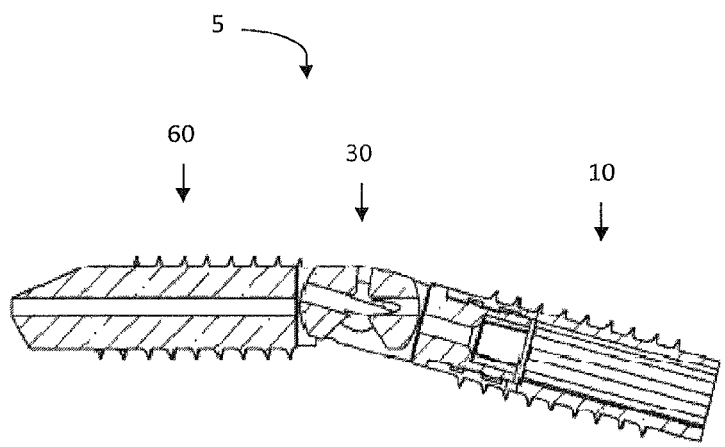

A fully assembled flexed bone fusion apparatus 5 is seen in FIGS. 32-33. The degree of flex is approximately 15 degrees off-axis, however as previously mentioned this particular embodiment is designed to flex as far as 30 degrees and still retain adequate strength at the joint. Both cross-section and external views are shown.

Example 2

Non-Cannulated Flexible Three-Part DIP Fusion Apparatus

Figure 7:
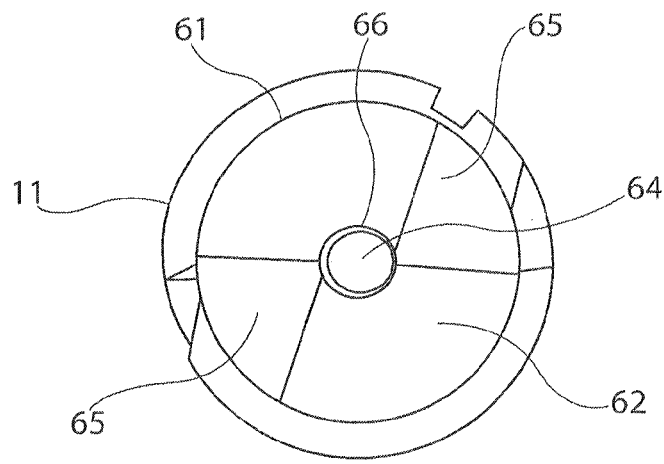
Figure 8:
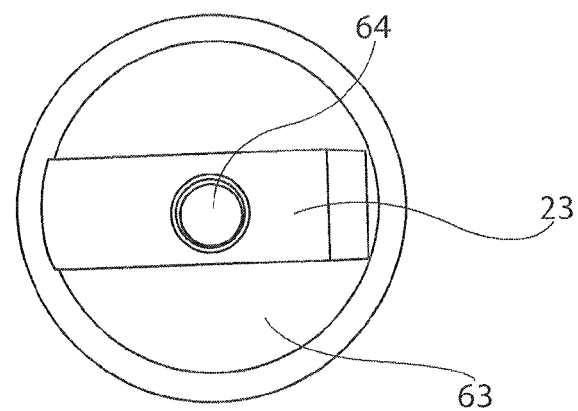

Another embodiment of the DIP fusion apparatus employs an anchor portion 60 that does not have a cannula that opens to the leading tip and so would not be used with a K-wire. However, a cannula may be utilized through the anchor attachment portion 21. No separate figure shows this embodiment since to remove the opening is adequately disclosed by description only. With respect to FIGS. 5-8, in this alternate embodiment the anchor lumen/cannula 64 in anchor locking wedge 23, anchor axial face 24 and continuing through the anchor annular groove 25 would still exist. The delivery tool alignment pin 105 would engage the anchor as before, via coupler and through at least the anchor locking wedge part of the attachment assembly 20 (FIG. 1). With reference to FIG. 7, the tip hole 66 shown in the anchor leading tip 62 would not be present in this embodiment.

Compressor tool 110 shown in FIGS. 23-24 is a non-cannulated delivery tool, and would be matched to this embodiment. However, the same delivery tool may also be used in a cannulated DIP fusion apparatus, as previously described in Example 1. In the same fashion, a compressor tool 110 either with or without a cannula may be used with this non-cannulated apparatus.

Example 3

Linear Two-Part Bone Fusion Apparatus

Another embodiment of the inventive concept disclosed herein is described and disclosed in FIGS. 28-31. In this embodiment the bone fusion apparatus does not flex about the coupler as the coupler's flex feature has been removed. Instead the apparatus comprises two components, an anchor portion and a compressor portion. This embodiment still accomplishes compression and fusion of two fractured parts or adjacent bones, although it has not been designed to flex about its longitudinal axis (long axis). The anchor portion is very similar to the anchor portion of the first example, although the trailing end has been modified to directly couple to the compressor portion. The compressor remains the same as the embodiments described in Example 1. Description of this embodiment is largely restricted to just those features that differ from the embodiments of Example 1, unless otherwise noted. If a feature is not noted in this example but it is visible in the Figures, then it is assumed to be substantially the same as the corresponding feature from the embodiments of Example 1.

The embodiment described above is directed to a bone fusion apparatus comprising an anchor portion comprising an elongated body with screw threads on at least a portion of its exterior, the anchor having a leading tip and a trailing end adapted for an axial rotation interface, the anchor trailing end also having a keyed driving pattern. "Axial rotation" is rotation about the transverse axis of the anchor and/or compressor portions as depicted by the rotating arrow in FIG. 1, which shows clockwise axial rotation about the axis of the assembled flexible bone fusion apparatus.

The second component is a compressor portion comprising an elongated body with screw threads of the same pitch and diameter on at least a portion of its exterior, the compressor having a trailing end and a leading end adapted for an axial rotation interface, the compressor trailing end also having a keyed driving pattern different from the anchor trailing end keyed driving pattern.

An interface between the compressor portion and the anchor portion joins the two, whereby either the anchor trailing end or the compressor leading end fit within the other longitudinally at a predetermined distance to allow axial rotation and longitudinal immobility. In one embodiment, the same snap-fit type interface may be used. However, other interfaces that allow axial freedom but longitudinal retention in place will be interchangeable with the snap-fit interface, and will be apparent to one having ordinary skill in the art.

Figure 28:
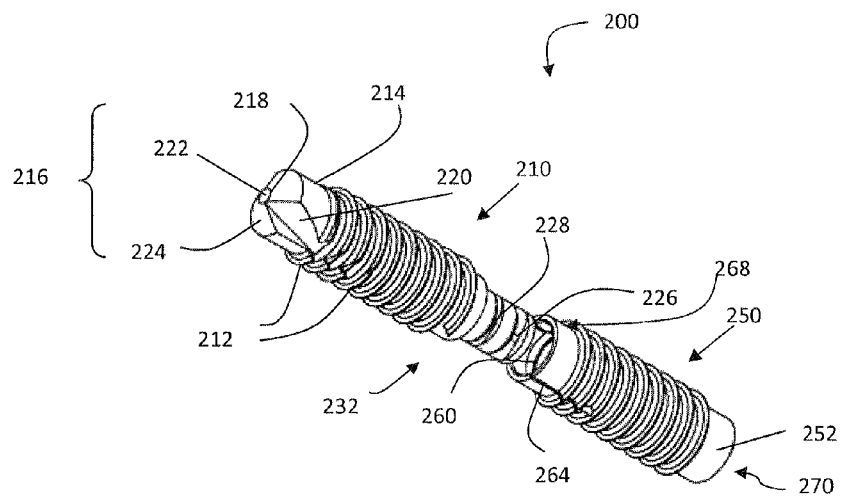
Figures 29A, 29B, 29C:
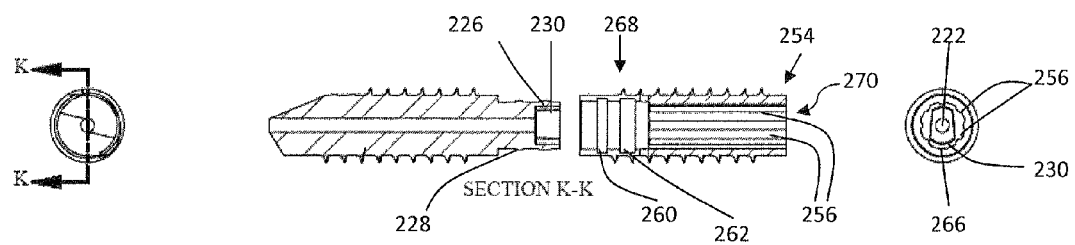
FIGS. 29A-C are horizontal isometric cross-sectional views of the exploded apparatus of FIG. 28.

With reference to FIGS. 28-31, linear two-part bone fusion apparatus 200 is depicted in computer-aided figures. FIG. 28 is an inclined exploded perspective view showing the anchor portion 210 in front, and the compressor portion 250 in the rear. Anchor portion has retaining means disposed on the external aspect of the anchor body 214, in this embodiment screw threads 212. Screw threads 212 are substantially the same pitch and diameter as on the trailing compressor portion 250. They are synchronized in the same manner as in the embodiments of Example 1, i.e. through alignment of the keyed driving patterns of compressor, coupler and delivery tool. Leading tip 216 has a tip hole 218 for access to the anchor lumen or cannula, 222. Leading tip 216 has a drill surface 224, a portion of which may be a tap edge surface 220 for cutting bone as previously disclosed. At the anchor trailing end 232 is an extension of the anchor body. In one embodiment the extension may have one or more external annular ridges 226, 228. The annular ridges 226, 228 engage with the compressor annular grooves 260, 262 found in the mating component surface, the internal diameter of the compressor leading end 268. The anchor trailing end 232 may also have a driving pattern for engaging with delivery tool. In this embodiment. FIG. 29*c* shows a compressor trailing end view down the lumen of the compressor which discloses the outline of the slot pattern 230 from the embodiments of Example 1 reproduced in this embodiment.

In this embodiment, compressor portion 250 is largely identical to the compressor portion of the embodiments of Example 1. Compressor portion 250 has a compressor body 252 having a compressor lumen 254 upon the surface of which is disposed a second driving pattern identical to that of the compressor lumen of Example 1. In similar manner the driving pattern includes longitudinal ridges octagonally arranged, with one ridge missing. The ridges are visible in the views of FIGS. 29*b*, 29*c*, 31*b* and 31*c* as elements 256. At the leading end 268 of the compressor portion 250 are found annular grooves 260, 262, mentioned previously. In this embodiment, an axial slot 264 has been cut in the compressor body to allow for a snap-fit. The compressor portion trailing end 270 is where the tools enter.

Figure 30:
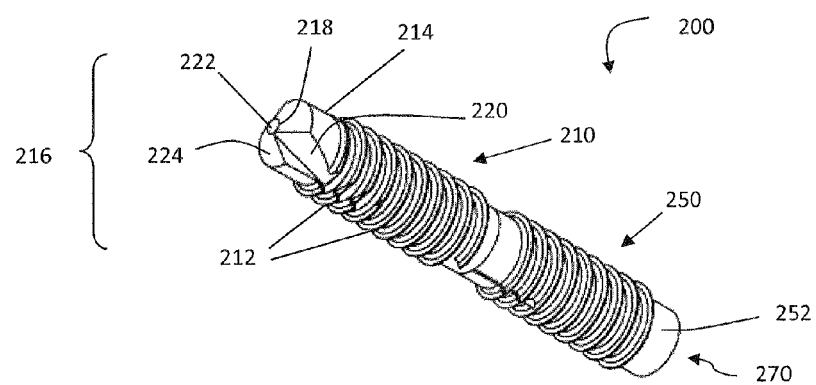
Figures 31A, 31B, 31C:
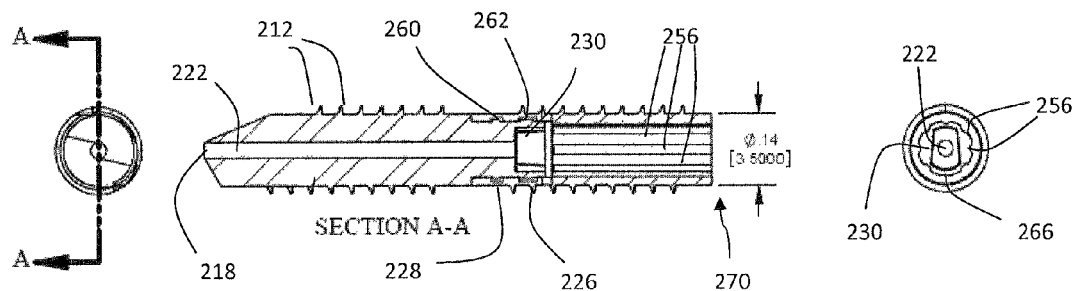
FIGS. 31A-C are horizontal isometric cross-sectional views of the assembled apparatus of FIG. 30.

The embodiment of FIGS. 30-31 shows the assembled two-part linear bone fusion apparatus.

The method of operating this bone fusion apparatus is again very similar. No separate delivery or compressor tools are disclosed because the same tools are also usable with this embodiment, with the exception that the delivery tool of FIGS. 23-24 (with the pin) will not be necessary due to the absence of a coupler and anchor to align. This apparatus, when assembled, is fully aligned and will not misalign on installation or thereafter. The same method of installation also works, with the exception that the step of flexing the coupler is not carried out.

Example 4

Method of Fusing Adjacent Bones or Fragments

A further embodiment of the inventive concept described herein is a method of fusing two adjacent bones or fragments to create a straight or non-linear post-fusion orientation of the bones. With reference to the figures, this is accomplished using an embodiment of the inventive apparatus comprising an anchor portion 60 having an elongated anchor body 61 with screw threads 11 on at least a portion of the anchor's exterior, the anchor having a leading tip 62 and an anchor end 63. The anchor portion 60 is joined through a coupler portion 30 to a compressor portion 10 having an elongated compressor body 12 with screw threads 11 of the same pitch and diameter on at least a portion of its exterior. Coupler 30 has a first end 31 adapted to rotatably engage the anchor 60 in a first plane, the coupler 30 also having a second end 32 adapted to rotatably engage the compressor 10 through axial rotation.

The second step is optional and involves preparing a channel in the adjacent bones through which the flexible bone fusion apparatus 5 is installed. Sometimes this is accomplished by K-wire guided drilling of the bone. The use of a K-wire to guide implantation is well-know and so is not elaborated upon here. Generally, if two adjacent bones are to be fused, then the K-wire is inserted through both bones along the axis of the bone fusion apparatus and a cannulated bone drill is used to create a channel. If a bone fracture is being repaired then the K-wire is similarly situated between the two bone fragments so as to locate the flexible bone fusion apparatus 5 optimally. If a K-wire is used then the cannulated version of the apparatus is indicated. Alternatively, a non-cannulated version of the flexible bone fusion apparatus 5 may be used in the appropriate circumstance such as when drilling is not feasible or use of a K-wire in unnecessary.

In this embodiment the next step is inserting the flexible bone fusion apparatus 5 through both bones while positioning the anchor-coupler interface at or near the natural joint location. In the embodiments described herein as specifically applied to a DIP fusion, insertion of the apparatus involves manually driving or screwing the DIP fusion apparatus through the appropriately prepared fingertip in a clockwise direction while orienting it into and down the pre-drilled channel of the distal phalange in the direction of the medial phalange. In one embodiment, installation starts with the anchor portion 60 being installed into the tip of the finger into and through the distal phalange. The threads 11 of the anchor portion 60 will widen the pre-drilled channel (or cut a new one if no pre-drilling step occurred) somewhat and have a diameter defined by the anchor body 61 and screw thread 11 diameters. About halfway through installation the anchor portion 60 will emerge from the distal end of the distal phalange and the leading tip 62 will begin to engage the medial phalange at its proximal end at or about its central medullary canal, and driving of the entire DIP fusion device will stop when the physician decides the apparatus is optimally located so that the coupler-anchor interface is between the phalanges at approximately the natural joint location and is aligned with the conical two-part interface oriented in a vertical direction.

In this embodiment the next step is flexing the coupler-anchor conical two-part interface to the desired degree of rotation. If the coupler-anchor has become locked during installation, then the interface is first unlocked by pushing the anchor and coupler towards the other, thereby freeing the anchor and coupler locking wedges 23, 26 respectively from their respective annular grooves 25, 28. The desired degree of rotation is then applied by bending the distal and medial phalanges to create a bent or flexed joint, and the precise alignment is then locked by pulling the anchor 60 and coupler 30 apart slightly. The physician will know when locking is accomplished because slight tugs will signal either way if the joint is immobilized or not.

In this embodiment the last step is compressing or bringing together the adjacent bones by reversing the rotation of the compressor portion 10 sufficiently to impart the desired amount of compression while maintaining the desired alignment of the adjacent bones at the joint area. To accomplish this step the delivery tool 100 is replaced with the compressor tool 110. Compressor tool 110 does not have a drive pattern for engaging the coupler, only one to engage the compressor. Thus the coupler-anchor orientation is not affected by the use of the compressor tool. After proper insertion and internal alignment of the compressor tool along the ridge-and-groove arrangement described previously, to move the distal phalange into direct contact counter-clockwise rotation is applied until the to degree of contact is sufficient.

Example 5

Method of Synchronizing Screw Threads

A further embodiment of the inventive concept is a method of maintaining screw thread synchronization in a bone fusion apparatus having a first screw thread on a leading component and a second screw thread on a trailing component, the two components being separated by a coupling non-threaded component, the screw threads having the same thread pitch. The method comprises providing separate driving patterns in the trailing and non-threaded component to coordinate the separate screw threads with each other such that a single driving tool having separate complementary driving patterns will facilitate coordination of the screw threads by synchronized alignment of the trailing and non-threaded components.

The embodiments of the invention also comprise kits that include one or more of the bone fusion apparatus of varying sizes and diameters to fit the application, delivery and compression tools, K-wires, drills and drill bits and a case for holding the tools and parts. Components of the kit may be sterile and/or sterilizable (e.g., autoclavable). In some examples, components of the kit, such as bone fusion apparatus and/or wires, may be intended for single use. In some examples, components of the kit, such as drills and/or drivers, may be intended or suitable for repeated use.

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

The invention claimed is:

1. A flexible bone fusion apparatus comprising:
    (a) an anchor having an elongated body with screw threads on at least a portion of its exterior, the anchor having a leading tip and an end;
    (b) a compressor having an elongated body with screw threads on at least a portion of its exterior, wherein the screw threads on the anchor and the screw threads on the compressor have a same pitch and diameter; and
    (c) a coupler having a first end adapted to rotatably engage the anchor in a first plane, the coupler also having a second end adapted to rotatably engage the compressor through axial rotation;
    wherein when assembled, an anchor attachment portion on the anchor and an interlocking coupler attachment portion on the coupler interlock to form an attachment assembly; wherein the anchor attachment portion comprises at least one locking wedge, at least one semi-circular conical face and at least one semi-circular annular groove; wherein the coupler attachment portion comprises at least one locking wedge, at least one semi-circular conical face and at least one semi-circular annular groove; and
    wherein the assembled attachment assembly can be into a specific angled orientation by exerting thrust on either the anchor or the coupler in a direction away from the other.

2. The apparatus of claim 1 wherein the coupler first end comprises an anchor end and the coupler second end comprises a compressor end, the anchor and coupler sharing an interface at which they may rotate in a first plane, the coupler and compressor sharing a second interface at which they rotate axially.

3. The apparatus of claim 1 wherein the anchor further comprises a lumen running an entire length of the anchor.

4. The apparatus of claim 1 wherein the compressor further comprises a lumen running an entire length of the compressor.

5. The apparatus of claim 4 wherein the compressor lumen is adapted to engage a delivery tool through a driving pattern.

6. The apparatus of claim 5 wherein the compressor lumen driving pattern comprises seven ridges and an area with an absence of a ridge, the seven ridges and the area spaced octagonally, so as to allow keying of axial orientation between the compressor and the delivery tool.

7. The apparatus of claim 1 wherein the coupler further comprises a lumen running an entire length of the coupler.

8. The apparatus of claim 1 wherein the anchor further comprises a tap edge on its leading tip.

9. The apparatus of claim 1 wherein the assembled attachment assembly can rotate in the first plane from approximately zero to thirty degrees in either direction.

10. The apparatus of claim 1 wherein the coupler has a lumen that is adapted to engage a delivery tool through a driving pattern.

11. The apparatus of claim 10 wherein the coupler lumen comprises a slot for receiving the delivery tool.

12. The apparatus of claim 1 wherein the coupler and compressor are joined by a snap-fit interface comprising at least one annular ridge in one of either the compressor or coupler, and at least one annular groove in the other of the compressor or coupler, the snap-fit interface adapted to allow relative axial rotation of the compressor and coupler.

13. The apparatus of claim 12 wherein the compressor comprises at least one annular groove located in a lumen and the coupler comprises at least one annular ridge located on an external diameter.

14. The apparatus of claim 12 wherein the snap-fit interface has at least one expansion slot cut through either the compressor body or coupler body.

15. The apparatus of claim 1 wherein the screw threads of the anchor and compressor are synchronized to provide a continuous thread pitch from anchor to compressor.

16. The apparatus of claim 1 wherein the first plane rotation direction varies from approximately zero to thirty degrees in either direction when fixed in final position.

17. A method of using the flexible bone fusion apparatus of claim 1, comprising the step of locking a configuration of the anchor and the coupler by reversing the axial rotation of the compressor until bones or bone fragments touch.

18. A method of fusing two adjacent bones to create a non-linear post-fusion orientation comprising:
   (a) providing a flexible bone fusion apparatus comprising:
      (i) an anchor having an elongated body with screw threads on at least a portion of its exterior, the anchor having a leading tip and an end;
      (ii) a compressor having an elongated body with screw threads on at least a portion of its exterior, wherein the screw threads on the anchor and the screw threads on the compressor have a same pitch and diameter; and
      (iii) a coupler having a first end adapted to rotatably engage the anchor in a first plane, the coupler also having a second end adapted to rotatably engage the compressor through axial rotation;
      wherein when assembled, an anchor attachment portion on the anchor and an interlocking coupler attachment portion on the coupler interlock to form an attachment assembly;
      wherein the anchor attachment portion comprises at least one locking wedge, at least one semi-circular conical face and at least one semi-circular annular groove;
      wherein the coupler attachment portion comprises at least one locking wedge, at least one semi-circular conical face and at least one semi-circular annular groove; and
      wherein the assembled attachment assembly can be locked into a specific angled orientation by exerting thrust on either the anchor or the coupler in a direction away from the other;
   (b) optionally preparing a channel in adjacent bones through which the flexible bone fusion apparatus is installed;
   (c) inserting the flexible bone fusion apparatus through both adjacent bones while positioning the attachment assembly at or near a natural joint location;
   (d) flexing the attachment assembly to a desired degree of flexion; and
   (e) compressing the adjacent bones by reversing the axial rotation of the compressor sufficiently to impart a desired amount of compression while maintaining a desired alignment of the adjacent bones.

\* \* \* \* \*

UNITED STATES PATENT AND TRADEMARK OFFICE
CERTIFICATE OF CORRECTION

| | | |
|---|---|---|
| PATENT NO. | : 8,529,611 B2 | Page 1 of 1 |
| APPLICATION NO. | : 13/049363 | |
| DATED | : September 10, 2013 | |
| INVENTOR(S) | : Champagne et al. | |

It is certified that error appears in the above-identified patent and that said Letters Patent is hereby corrected as shown below:

In the claims

Claim 1, Col. 20, line 42, "be into" should be --be locked into--.

Signed and Sealed this
Twenty-sixth Day of August, 2014

Michelle K. Lee
*Deputy Director of the United States Patent and Trademark Office*